United States Patent
Sarrias Fornés et al.

(10) Patent No.: US 11,370,844 B2
(45) Date of Patent: Jun. 28, 2022

(54) ANTI-CD5L ANTIBODY AND USES THEREOF

(71) Applicant: FUNDACIÓ INSTITUT D'INVESTIGACIÓ EN CIÈNCIES DE LA SALUT GERMANS TRIAS I PUJOL, Badalona (ES)

(72) Inventors: Maria Rosa Sarrias Fornés, Barcelona (ES); Lucía Sanjurjo Bouza, Ferrol (ES); Gemma Aran Canals, Ripollet (ES)

(73) Assignee: FUNDACIÓ INSTITUT D'INVESTIGACIÓ EN CIÈNCIES DE LA SALUT GERMANS TRIAS I PUJOL, Bad Alona (ES)

(*) Notice: Subject to any disclaimer, the term of this patent is extended or adjusted under 35 U.S.C. 154(b) by 146 days.

(21) Appl. No.: 16/760,179

(22) PCT Filed: Oct. 30, 2018

(86) PCT No.: PCT/EP2018/079751
§ 371 (c)(1),
(2) Date: Apr. 29, 2020

(87) PCT Pub. No.: WO2019/086480
PCT Pub. Date: May 9, 2019

(65) Prior Publication Data
US 2020/0354467 A1 Nov. 12, 2020

(30) Foreign Application Priority Data
Oct. 30, 2017 (EP) ...................................... 17382725

(51) Int. Cl.
*C07K 16/28* (2006.01)
*A61P 37/04* (2006.01)
(Continued)

(52) U.S. Cl.
CPC ...... *C07K 16/2896* (2013.01); *A61K 39/3955* (2013.01); *A61K 45/06* (2013.01);
(Continued)

(58) Field of Classification Search
CPC . C07K 16/2896; C07K 2317/76; A61P 37/04; A61P 35/00; A61K 39/3955;
(Continued)

(56) References Cited

U.S. PATENT DOCUMENTS
2020/0113462 A1   4/2020   Martínez Piñeiro et al.

FOREIGN PATENT DOCUMENTS
WO    WO 98/39443 A1 *  3/1998  ............ C12N 15/12
WO    98/39443 A1      9/1998

OTHER PUBLICATIONS

Tomita, T., et al. (2017) Apoptosis inhibitor of macrophage ameliorates fungus-induced peritoneal injury model in mice. Scientific Reports 7: 6450. (Year: 2017).*

(Continued)

*Primary Examiner* — Joanne Hama
*Assistant Examiner* — Audrey L Buttice
(74) *Attorney, Agent, or Firm* — Seed IP Law Group LLP

(57) ABSTRACT

The invention relates to a CD5L-binding agent or a pharmaceutical composition thereof for use in the treatment of cancer by inhibiting macrophage M2 activation or promoting lymphocyte activation.

12 Claims, 5 Drawing Sheets

Specification includes a Sequence Listing.

(51) Int. Cl.
  *A61P 35/00* (2006.01)
  *A61K 39/395* (2006.01)
  *A61K 45/06* (2006.01)
  *A61K 39/00* (2006.01)
(52) U.S. Cl.
  CPC .............. *A61P 35/00* (2018.01); *A61P 37/04* (2018.01); *A61K 2039/505* (2013.01); *C07K 2317/76* (2013.01)
(58) Field of Classification Search
  CPC ............. A61K 45/06; A61K 2039/505; G01N 33/574; G01N 2333/70596
  See application file for complete search history.

(56) References Cited

OTHER PUBLICATIONS

Hao, N., et al. (2012) Macrophages in Tumor Microenvironments and the Progression of Tumors Clinical and Developmental Immunology Article 948098 (Year: 2012).*
Genin et al. (2015) M1 and M2 macrophages derived from THP-1 cells differentially modulate the response of cancer cells to etoposide BMC Cancer 15(577) (Year: 2015).*
Li, Y., et al. (2011) Api6/AIM/Spa/CD5L Overexpression in Alveolar Type II Epithelial Cells Induces Spontaneous Lung Adenocarcinoma Cancer Research 71(16): 5488-5499 (Year: 2011).*
Emmons, K. M., et al (2017) Realizing the Potential of Cancer Prevention—The Role of Implementation Science N Engl J Med 376 (10); 986-990 (Year: 2017).*
Cuzick, J. (2017) Preventive therapy for cancer Lancet Oncol 18; e472- e482 (Year: 2017).*
Kashmiri, S. et al. (2005) SDR grafting—a new approach to antibody humanization Methods 36(1); 25-34 (Year: 2005).*
Kratochvill, F., et al. (2015) TNF counterbalances the emergence of M2 tumor macrophages Cell Rep 12(11): 1902-1914. (Year: 2015).*
Denis, G.V and M.S. Obin (2012) 'Metabolically healthy obesity': Origins and implications. Molecular Aspects of Medicine 34(1): 59-70. (Year: 2012).*
Miyazaki, T., et al. (2011) AIMing at Metabolic Syndrome—Towards the Development of Novel Therapies for Metabolic Diseases via Apoptosis Inhibitor of Macrophage (AIM). Circulation Journal 75: 2522-2531. (Year: 2011).*
Nishikido, T., et al. (2016) Deletion of Apoptosis Inhibitor of Macrophage (AIM)/CD5L Attenuates the Inflammatory Response and Infarct Size in Acute Myocardial Infarction. Journal of American Heart Association. (Year: 2016).*
Liu, C. et al, (2013) M2-polarized tumor-associated macrophages promoted epithelial-mesenchymal transition in pancreatic cancer cells, partially through TLR4/IL-10 signaling pathway Laboratory Investigation 93: 844-854. (Year: 2013).*
Sanjurjo, L., et al. (2015) The human CD5L/AIM-CD36 axis: A novel autophagy inducer in macrophages that modulates inflammatory responses Autophagy. 11(3): 487-502. (Year: 2015).*
Sanjurjo, L., et al. (2015) AIM/CD5L: a key protein in the control of immune homeostasis and inflammatory disease Journal of Leukocyte Biology 98: 173-184 (Year: 2015).*
Chik, W. et al. (2010) Purification and Cytotoxicity Assay of Tomato (*Lycopersicon esculen* turn) Leaves Methanol Extract as Potential Anticancer Agent Journal of Applied Sciences 10(24): 3283-3288 (Year: 2010).*
Funfrock, P. (2020) How are mouse monoclonal antibodies humanized: current approaches and limitations Proteo Blog by ProteoGenix (Year: 2020).*
U.S. Appl. No. 16/757,263, filed Apr. 17, 2020.
Amézaga et al., "Human scavenger protein AIM increases foam cell formation and CD36-mediated oxLDL uptake," *Journal of Leukocyte Biology* 95:509-520, 2014.
Bastos-Amador et al., "Proteomic analysis of microvesicles from plasma of healthy donors reveals high individual variability," *Journal of Proteomics* 75:3574-3584, 2012.
Maehara et al., "Circulating AIM Prevents Hepatocellular Carcinoma through Complement Activation," *Cell Reports* 9:61-74, 2014.
Mantovani et al., "Macrophages, innate immunity and cancer: balance, tolerance, and diversity," *Current Opinion in Immunology* 22:231-237, 2010.
Martinez et al., "The macrophage soluble receptor AIM/Api6/CD5L displays a broad pathogen recognition spectrum and is involved in early response to microbial aggression," *Cellular & Molecular Immunology* 77:343-354, 2014.
Novus, "CD5L Antibody (1C8)", (Jan. 1, 2017), URL: https://www.novusbio.com/products/cd51-antibody-1c8_h00000922-m01, (Nov. 30, 2017), XP055430631.
Sanjurjo et al., "AIM/CD5L: a key protein in the control of immune homeostasis and inflammatory disease," *Journal of Leukocyte Biology* 98(2): 173-184, 2015.
Sanjurjo et al., "The human CD5L/AIM-CD36 axis: A novel autophagy inducer in macrophages that modulates inflammatory responses," *Autophagy* 77(3):487-502, 2015.

* cited by examiner

A

B

ANTI-CD5L ANTIBODY AND USES THEREOF

This application claims the benefit of European Patent Application EP17382725.4 filed on Oct. 30, 2017.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 370088_402USPC_SEQUENCE_LISTING.txt. The text file is 13.5 KB, was created on Apr. 29, 2020, and is being submitted electronically via EFS-Web.

TECHNICAL FIELD

The present invention in general relates to the field of immunotherapy. In particular, the invention relates to the use of anti-CD5L antibodies for the modulation of macrophage activation with therapeutic purposes. The antibodies of the invention are particularly useful in cancer immunotherapy.

BACKGROUND ART

The tumor microenvironment is a complex system composed of many cell types including endothelial cells, smooth muscle cells, fibroblasts, and inflammatory cells such as macrophages and dendritic cells. Macrophages are the major inflammatory components of the tumor stroma, and they are defined as tumor-associated macrophages (TAMs). TAMs have the capacity to shift their functional phenotypes in response to various microenvironmental signals generated from tumor and stromal cells.

The functional phenotypes that macrophages can acquire are generally classified as classical M1 activation or alternative M2 activation. M1 macrophages are characterized by their powerful pro-inflammatory and cytotoxic activity, thus, they can kill pathogens (bacteria, virus and protozoa) and tumor cells. For this reason, they are often regarded as anti-tumoral macrophages. M2 macrophages are known to have anti-inflammatory or resolutive functions such as angiogenesis promotion or tissue repair. Moreover, they are known to support tumor growth and progression; hence, they are commonly considered pro-tumoral macrophages. As reported by Mantovani A. and colleagues (cf. Mantovani et al. in "Macrophages, innate immunity and cancer: balance, tolerance, and diversity", Curr Opin Immunol. 2010 April; 22(2):231-7), TAMs usually present an immunosuppressive M2 phenotype.

In recent years, TAMs have emerged as a potential target for cancer immunotherapy due to their ability to modulate cancer cell biology and the response of other immune cells per se or in response to treatment. Likewise, TAMs (and their activation status) are now being recognized as potential biomarkers for diagnosis and prognosis of cancer.

In an attempt to further understand macrophage behavior, John A. Gebe et al. reported in the patent application WO9839443 the identification of CD5L. In this prior art, the authors speculate about the possible role of CD5L in macrophage's adherence and trafficking, with no experimental data supporting such conclusions.

In spite of the efforts hitherto made, there is a lack of reliable and efficient markers to identify the different populations of macrophages in humans; and, on the other hand, there is an incomplete understanding of the molecular players involved in macrophage activation and their precise contribution to the process. These drawbacks have limited, in a great extent, the development of cancer immunotherapies.

In view of the above, there is still a need for developing further anticancer approaches.

SUMMARY OF INVENTION

The present inventors have unveiled a new and unexpected role of CD5L during macrophage M2 activation.

As shown in the examples below, the inventors found that CD5L expression is strongly induced during the M2 activation process (see FIG. 1). Therefore, it constitutes a novel molecular marker to identify M2 macrophage populations.

More importantly, it was found that CD5L actively contributes to the acquisition of an M2-like molecular and functional phenotype by acting as an M2-driver. As shown below (see FIG. 2), addition of recombinant CD5L to primary cell cultures of human macrophages is enough to induce the acquisition of an M2 phenotype.

Additionally, the inventors discovered that CD5L is not only capable of triggering the M2 activation process, but also it is necessary for the process to take place. Thus, it is the first time that it is reported that CD5L plays an essential role in macrophage M2 polarization.

Surprisingly, the inventors found that when CD5L was depleted in M2-like macrophages by contacting them with a CD5L-binding agent, such as an antibody, the immunosuppressive M2 phenotype was inhibited (see FIG. 3 A). Moreover, it was found that the inflammatory response of M2 macrophages to LPS could be restored when they were treated with a CD5L-binding agent, such as the anti-CD5L antibody (see FIG. 3 B).

The role of CD5L in macrophage's polarization reported by the present inventors is unexpected in the light of the prior art (WO9839443). In this prior art, CD5L was suggested to be a positive effector of the inflammatory response. Moreover, it was suggested that blocking CD5L activity by anti-CD5L antibodies would prevent macrophages' pro-inflammatory activity. However, no minimum experimental data supporting such conclusion were provided. Thus, such suggestion was more a mere hypothesis drawn from tests that were hardly related to the inflammation process.

Therefore, the results herein provided revealed that CD5L-binding agents, such as anti-CD5L antibodies, have the opposite effect on the immune response as previously thought—they favor, not prevent, pro-inflammatory responses.

Altogether, in the examples provided below the inventors have demonstrated the utility of blocking CD5L activity to prevent M2 activation by developing a particular monoclonal antibody against CD5L.

Thus, in a first aspect the present invention provides an anti-CD5L monoclonal antibody or a CD5L-binding fragment thereof comprising a VH CDR3 of sequence SEQ ID NO: 1 and a VL CDR3 of sequence SEQ ID NO: 2. Preferably, such an anti-CD5L monoclonal antibody or a CD5L-binding fragment thereof comprises a VH sequence comprising, in the following specified order: a CDR1 of sequence SEQ ID NO: 3 or a humanized variant thereof, a CDR2 of sequence SEQ ID NO: 4 or a humanized variant thereof, and a CDR3 of sequence SEQ ID NO: 1 or a humanized variant thereof; and a VL sequence comprising, in the following specified order: a CDR1 of sequence SEQ ID NO: 5 or a humanized variant thereof, a CDR2 of sequence SEQ ID NO: 6 or a humanized variant thereof, and a CDR3 of sequence SEQ ID NO: 2 or a humanized variant thereof.

In a further aspect, the present invention provides a conjugate comprising the antibody or the CD5L-binding fragment thereof of the first aspect.

In a second aspect the present invention provides a kit of parts comprising (a) an antibody or an CD5L-binding fragment thereof as defined in the first aspect of the invention; and (b) optionally, instructions for its use.

In a third aspect the present invention provides the antibody or the CD5L-binding fragment thereof according to the first aspect of the invention, or alternatively, the conjugate according to a further aspect of the invention, for use in therapy, diagnosis or prognosis.

In a fourth aspect the present invention provides a pharmaceutical composition comprising a therapeutically effective amount of a CD5L-binding agent together with one or more pharmaceutically acceptable carriers or excipients.

In a fifth aspect the present invention provides a kit of parts comprising (a) a CD5L-binding agent or a pharmaceutical composition according to the fourth aspect of the invention; (b) a drug; and (c) optionally instructions for its use.

As shown in the examples below, the inventors have demonstrated the utility of blocking CD5L activity to prevent M2 activation by using a monoclonal antibody against CD5L. However, it falls within reason that any antibody or any other agent capable of binding CD5L (a peptide, a small molecule, etc.), which is commercially available, can also be useful in the prevention of macrophage M2 activation.

Thus, in a sixth aspect the present invention provides a CD5L-binding agent, or an antibody or fragment thereof as defined in the first aspect, or a conjugate as defined in a further aspect, or a pharmaceutical composition as defined in the fourth aspect, or a kit as defined in the second or fifth aspect of the invention for use in inhibiting macrophage M2 activation, or alternatively, for use in promoting lymphocyte T activation.

It is well established in the art that M2 macrophages favor tumor progression and tumor growth (Mantovani A. et al., supra). Therefore, the new strategies herein provided for inhibiting M2 activation are a promising tool in the field of anticancer treatments by inhibiting M2 activation.

Furthermore, the inventors have found that by modulating CD5L activity in lymphocytes T they could control their level activation, as can be seen in FIG. 6. It is known in the art that lymphocytes T are a crucial component of the adaptive immune system with a particular importance in the control of tumours. Thus, the antibody of the invention is a promising tool for the treatment of tumors through the promotion of lymphocyte T activation.

Thus, in a seventh aspect the present invention provides a CD5L-binding agent, or an antibody or fragment thereof as defined in the first aspect, or a conjugate as defined in a further aspect, or a pharmaceutical composition as defined in the fourth aspect, or a kit as defined in the second or fifth aspect of the invention for use in the treatment and/or prevention of cancer. This aspect can also be formulated as the use of a CD5L-binding agent, or an antibody or fragment thereof as defined in the first aspect, or a conjugate as defined in a further aspect, or a pharmaceutical composition as defined in the fourth aspect of the invention for the manufacture of a medicament for the treatment and/or prevention of cancer. This aspect can also be formulated as a method for treating and/or preventing cancer, the method comprising administering a therapeutically effective amount of a CD5L-binding agent, or of an antibody or fragment thereof as defined in the first aspect, or a conjugate as defined in a further aspect, or a pharmaceutical composition as defined in the fourth aspect, to a subject in need thereof. As regards the plausibility of this aspect, and as illustrated in FIG. 5, it seems clear that targeting CD5L reduced tumor growth in a pre-clinical model of lung cancer. in addition, TAM polarization towards an M2 phenotype has been associated to bad prognosis in a wide variety of cancers, such as: glioblastoma, glioma, lung adenocarcinoma, lung squamous cell carcinoma, ovarian adenocarcinoma, hepatocellular carcinoma, head and neck squamous cell carcinoma, pancreatic adenocarcinoma, kidney papillary cell carcinoma, prostate adenocarcinoma, thyroid carcinoma, HPV-related cervical carcinoma, diffuse large B cell lymphoma, and breast carcinoma. Therefore, targeting CD5L for cancer immunotherapy should be a reasonable therapeutic option in light of the information and results provided in the present specification.

In an eighth aspect the present invention provides a CD5L-binding agent, or an antibody or fragment thereof as defined in the first aspect, or a conjugate as defined in a further aspect, or a pharmaceutical composition as defined in the fourth aspect, or a kit as defined in the second or fifth aspect of the present invention for use in combination therapy with an anticancer agent in the treatment and/or prevention of cancer. This aspect can also be formulated as the use of a CD5L-binding agent, or an antibody or fragment thereof as defined in the first aspect, or a conjugate as defined in a further aspect, or a pharmaceutical composition as defined in the fourth aspect for the manufacture of a medicament for use in combination therapy with an anticancer agent in the treatment and/or prevention of cancer in a patient. This aspect can also be formulated as a method for treating and/or preventing cancer, the method comprising administering a therapeutically effective amount of a CD5L-binding agent, or an antibody or fragment thereof as defined in the first aspect, or a conjugate as defined in the further aspect, or a pharmaceutical composition as defined in the fourth aspect of the present invention, in combination with an anticancer agent, to a subject in need thereof.

As mentioned above, the inventors have found that CD5L constitutes a novel molecular marker to identify M2 macrophage populations. And, in addition, it has been found that CD5L is expressed by tumor associated macrophages (TAMs), and its expression levels are positively correlated with the bad prognosis of cancer (see FIG. 4).

From the experimental data provided herein, it can be concluded that CD5L, when identified in a macrophage population, is indicative of cancer and depending on the evolution of the level of the marker, it provides useful information about prognosis.

Surprisingly, the inventors found that CD5L can be specifically localized on the surface of macrophages. This contrasts with the previous assumption that CD5L was a secreted soluble protein only located in the extracellular medium.

Thus, in a ninth aspect the present invention provides an in vitro method for determining the diagnosis or prognosis of a subject having cancer, the method comprising the step of determining the amount of CD5L in macrophages in an isolated biological sample of the subject.

The invention also provides an in vitro method for determining the diagnosis/prognosis and treating a subject suffering cancer, the method comprising the steps of determining the amount of CD5L in macrophages in an isolated biological sample of the subject, and initiating a suitable cancer treatment regimen for the subject if the level determined in step (b) is higher than the reference control level.

In a tenth aspect the present invention provides the use of CD5L as a diagnostic or prognostic marker of cancer, or as a marker for monitoring cancer, in an isolated macrophage-comprising biological sample.

In an eleventh aspect the present invention provides the use of means for determining the amount of CD5L in macrophages in an isolated biological sample of the subject for the diagnosis or prognosis of cancer in the method of the ninth aspect of the invention.

In a twelfth aspect, the present invention provides a method is for deciding or recommending to initiate a medical regimen in a subject, which method comprises the step (a) determining in vitro the amount of CD5L in macrophages in an isolated biological sample of the subject.

In a thirteenth aspect, the present invention provides a method for determining the efficacy of a medical regimen in a patient already diagnosed of cancer, the method comprising the steps of:

(a) in vitro measuring the amount of CD5L in macrophages in an isolated biological sample of the subject prior to the administration of the medical regimen;

(b) in vitro measuring the amount of CD5L in macrophages in an isolated biological sample of the subject once started the administration of the medical regimen; and (c) comparing the levels measured in steps (a) and (b), in such a way that if the amount of CD5L in macrophages measured in step (b) is lower than the amount of CD5L in macrophages measured in step (a), it is indicative that the medical regimen is effective in the treatment of cancer;

or, alternatively, the method comprising the steps of (i) in vitro measuring the amount of CD5L in macrophages in an isolated biological sample of the subject once started the administration of the medical regimen; and (ii) comparing the level measured in step (i) with a reference control level of the CD5L in macrophages, wherein, if the amount of CD5L in macrophages measured in step (i) is not higher than the reference control level, it is indicative that the medical regimen is effective in the treatment of cancer.

In a fourteenth aspect, the present invention provides an in vitro method for determining the presence of M2 macrophages in an isolated sample from a subject, the method comprising the step of determining the amount of CD5L in macrophages from the sample.

In a fifteenth aspect, the present invention provides the use of CD5L as a marker of M2 macrophages.

In a further aspect, the present invention provides an anticancer compound for use in a method of treatment of a patient with cancer, wherein the method comprises (i) determining the amount of CD5L in macrophages from an isolated biological sample from the patient; and (ii) if the amount of CD5L in macrophages of the test sample is higher than a reference value, administering to the patient an effective amount of the anticancer drug.

(B) LLC tumor growth curves measured on control (n=5) and anti-CD5L moAb-treated mice (n=4) (normalized to day 7 of experiment). P value was calculated using the Mann-Whitney test (*$p≤0.05$).

Figure 6:
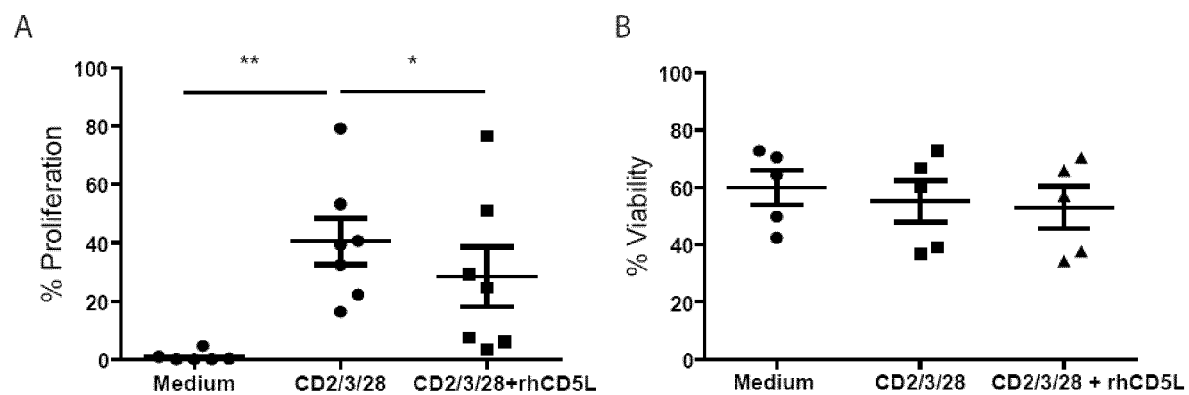

FIG. 6. rhC5L inhibits T cell proliferation Graphs showing % proliferation (A) and % viability (B) of T cells, in control (medium), stimulated (CD2/3/28), or stimulated in the presence of rhCD5L (1 µg/ml), for n=5-7 different healthy donors. P value was calculated using the paired t test (*p≤0.05; **p≤0.01)

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

As above exposed, the invention provides an anti-CD5L monoclonal antibody or a CD5L-binding fragment thereof, optionally comprising VH CDRs and VL CDRs of specific sequences or humanized variants thereof, in a specified order.

The skilled in the art would understand that "in the specified order" only refers to the order of the CDRs, and it does not exclude that other sequences are located between said CDRs.

The antibody of the invention has certain advantages as being monoclonal, e.g., reproducibility and large-scale production, that makes them suitable for clinical treatment.

The term "CD5L" as used herein refers to the soluble protein named CD5 antigen-like, Apoptosis inhibitor 6 (Api-6), Soluble protein alpha (Spalpha), Apoptosis inhibitor expressed by macrophages (AIM), CT-2, or IgM-associated peptide, which belongs to the scavenger receptor cysteine-rich (SRCR) superfamily. The protein sequence from several species is available in several protein databases, such as in Uniprot O43866_HUMAN *Homo sapiens*; Q9QWK4_MOUSE *Mus musculus*; A6QNW7_BOVIN *Bos taurus*; F7FUB7_MACMU *Macaca mulatta*, Q4KM75_RAT *Rattus norvegicus*; H2Q0B2_PANTR Pan troglodytes; F7HDX2_CALJA *Callithrix jacchus*; F1PAX5_CANLF *Canis lupus familiaris*; HOUZM6_CAVPO *Cavia porcellus;* G3R058_GORGO Gorilla gorilla gorilla; F1RN76_PIG *Sus scrofa*; A0A1E1GEV5_FELCA *Felis catus*; F7BXD8_HORSE *Equus caballus*.

An "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region (CH). The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

A "humanized variant" of a CDR, as used herein, refers to a murine CDR (recipient CDR) in which one or more residues are replaced by residues from a human CDR (donor CDR), wherein the resulting CDR maintains the binding capability of the recipient CDR. Humanized variants of CDRs have the advantage of lowering the risk of eliciting human anti-murin antibody response in patients. Methods for generating humanized variants of CDRs are well-known in the state of the art, for example, SDR grafting (Kashmiri S V et al., "SDR grafting—a new approach to antibody humanization" Methods. 2005, vol. 36(1), pp. 25-34). A humanized variant of a CDR may form part of a humanized antibody.

As used herein, the term "anti-CD5L antibody" referred in the first aspect of the invention, concerns to an antibody that binds to CD5L and that preferably comprises the VH CDR1, VH CDR2, VH CDR3, VL CDR1, VL CDR2 and VL CDR3, or humanized versions thereof, in their specified order. The antibody can be dimeric, trimeric, multimeric, bispecific, chimeric, human, humanized, murine, monkey, rat, hamster, rabbit and even frog, chicken, recombinant or engineered. In one embodiment, the antibody of the first aspect of the invention is of IgG or IgM class. In another embodiment, the subclass of the antibody of the first aspect of the invention is selected from the group consisting of IgG1, IgG2a, IgG2b and IgG3. In another embodiment, the antibody is of IgG2a subclass. In a particular embodiment, the antibody is a chimeric, humanized, or bispecific antibody.

As used herein "bispecific" or "bifunctional" antibody, refers to an artificial hybrid antibody having two different heavy/light chain pairs and two different binding sites. Bispecific antibodies can be produced by a variety of methods including fusion of hybridomas. See for example, Kostelny S A. et al., "Formation of a bispecific antibody by the use of leucine zippers", J Immunol. 1992, vol. 148(5), pp. 1547-53.

The term "chimeric" antibody refers to an antibody in which a portion of the heavy and/or light chain is derived from a particular source or species, while the remainder of the heavy and/or light chain is derived from a different source or species, typically a murine species.

A "humanized" antibody is a molecule of immunoglobulin, immunoglobulin chain or fragments thereof (such as Fv, Fab, Fab', F(ab')$_2$ or other antigen-binding subsequences of antibodies) which contains sequence(s) derived from a human immunoglobulin and sequence(s) derived from a non-human immunoglobulin and has the same or significantly similar epitope targeting capacity of the non-human immunoglobulin. In some instances, Fv framework residues of the human immunoglobulin are replaced by corresponding non-human residues. Humanized antibodies may also comprise residues which are found neither in the human antibody nor in the non-human CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Humanized antibodies may or may not include humanized variants of the CDRs. Methods for humanizing non-human antibodies are well known in the art (Safdari Y. et al., "Antibody humanization methods—a review and update" Biotechnol Genet Eng Rev. 2013, vol. 29, pp. 175-86) (Presta L G et al., "Antibody engineering", Curr Opin Biotechnol. 1992, vol. 3(4), pp. 394-8).

The skilled in the art knows computer programs or algorithms that allow obtaining in an automatic manner the humanized sequence of a given antibody, for instance the antibody of the invention.

The term "CD5L-binding fragment thereof" referred in the first aspect of the invention, also encompasses any part of an anti-CD5L-antibody having the sequences SEQ ID NO: 1 and 2, to bind and block CD5L. Suitable fragments include F(ab), F(ab') and Fv. A way to test if a fragment maintains the ability of binding and blocking CD5L can be performed, for example, by macrophage in vitro polarization test, as described in the examples below. Briefly, the CD5L-binding fragment is added along with an M2-inducer cytokine, such as IL10 (although any other can be used instead) to macrophage-like cells, such as PB monocytes, THP1 cells, U937 cells or K562 cells, and then the mRNA expression levels of one or more of the macrophage activation markers VEGF, CD163, and Mertk are measured. The skilled person can design appropriate primers to determine the level of expression of the activation markers. Illustrative non-(imitative examples of such primers are sequences SEQ ID NO: 17 to 20 and 25 to 26. The same steps have to be performed with the whole anti-CD5L antibody. And then the mRNA expression levels induced by the fragment and the whole antibody are compared: if the level of expression is similar for each activation marker, this will be indicative that the fragment maintains the ability of binding and blocking CD5L.

In one embodiment of the first aspect of the invention, the antibody or the CD5L-binding fragment thereof further comprises a VH CDR1 of sequence SEQ ID NO: 3, a VH CDR2 of sequence SEQ ID NO: 4, a VL CDR1 of sequence SEQ ID NO: 5, and a VL CDR2 of sequence SEQ ID NO: 6. Preferably, in the antibody or the CD5L-binding fragment thereof referred in the first aspect of the invention, the VH sequence comprises, in the following specified order: a CDR1 sequence having at least 85% identity with SEQ ID NO: 3, a CDR2 sequence having at least 85% identity with SEQ ID NO: 4, and a CDR3 sequence having at least 85% identity with SEQ ID NO: 1; and the VL sequence comprises, in the following specified order, a CDR1 sequence having at least 85% identity with SEQ ID NO: 5, a CDR2 of sequence SEQ ID NO: 6, and a CDR3 sequence having at least 85% identity with SEQ ID NO: 2. In another embodiment of the first aspect of the invention, in said antibody or the CD5L-binding fragment thereof, the VH sequence comprises, in the following specified order, a CDR1 of sequence SEQ ID NO: 3, a CDR2 of sequence SEQ ID NO: 4, and a CDR3 of sequence SEQ ID NO: 1; and the VL sequence comprises, in the following specified order, a CDR1 of sequence SEQ ID NO: 5, a CDR2 of sequence SEQ ID NO: 6, and a CDR3 of sequence SEQ ID NO: 2.

In another particular embodiment, optionally in combination with any of the embodiments provided above or below, the antibody or the CD5L-binding fragment thereof according to the first aspect:

the VH sequence has a sequence identity of 85%, 86%, 87%, 88%, 89%, 90%, 91%, 92%, 93%, 94%, 95%, 96%, 97%, 98%, 99% or 100% with SEQ ID NO: 7; or alternatively, the VL sequence has a sequence identity of 85%, 86%, 87%, 88%, 89%, 90%, 91%, 92%, 93%, 94%, 95%, 96%, 97%, 98%, 99% or 100% with SEQ ID NO: 8; or, alternatively, the VH sequence has a sequence identity of 85%, 86%, 87%, 88%, 89%, 90%, 91%, 92%, 93%, 94%, 95%, 96%, 97%, 98%, 99% or 100% with SEQ ID NO: 7 and the VL domain consisting of a sequence that has a sequence identity of 85%, 86%, 87%, 88%, 89%, 90%, 91%, 92%, 93%, 94%, 95%, 96%, 97%, 98%, 99% or 100% with SEQ ID NO: 8.

In the present invention the term "identity" refers to the percentage of residues that are identical in the two sequences when the sequences are optimally aligned. If, in the optimal alignment, a position in a first sequence is occupied by the same amino acid residue as the corresponding position in the second sequence, the sequences exhibit identity with respect to that position. The level of identity between two sequences (or "percent sequence identity") is measured as a ratio of the number of identical positions shared by the sequences with respect to the size of the sequences (i.e., percent sequence identity=(number of identical positions/total number of positions)×100).

A number of mathematical algorithms for rapidly obtaining the optimal alignment and calculating identity between two or more sequences are known and incorporated into a number of available software programs. Examples of such programs include the MATCH-BOX, MULTAIN, GCG, FASTA, and ROBUST programs for amino acid sequence analysis, among others. Preferred software analysis programs include the ALIGN, CLUSTAL W, and BLAST programs (e.g., BLAST 2.1, BL2SEQ, and later versions thereof).

For amino acid sequence analysis, a weight matrix, such as the BLOSUM matrixes (e.g., the BLOSUM45, BLOSUM50, BLOSUM62, and BLOSUM80 matrixes), Gonnet matrixes, or PAM matrixes (e.g., the PAM30, PAM70, PAM120, PAM160, PAM250, and PAM350 matrixes), are used in determining identity.

The BLAST programs provide analysis of at least two amino acid sequences, either by aligning a selected sequence against multiple sequences in a database (e.g., GenSeq), or, with BL2SEQ, between two selected sequences. BLAST programs are preferably modified by low complexity filtering programs such as the DUST or SEG programs, which are preferably integrated into the BLAST program operations. If gap existence costs (or gap scores) are used, the gap existence cost preferably is set between about −5 and −15. Similar gap parameters can be used with other programs as appropriate. The BLAST programs and principles underlying them are further described in, e.g., Altschul et al., "Basic local alignment search tool", 1990, J. Mol. Biol, v. 215, pages 403-410. A particular percentage of identity encompasses variations of the sequence due to conservative mutations of one or more amino acids leading to an antibody or CD5L-binding fragment thereof being still effective, thus able to bind CD5L epitopes. Protein variations are also due to insertions or deletions of one or more amino acids.

In a more particular embodiment of the first aspect of the invention, the antibody or the CD5L-binding fragment thereof comprises:

a VH of sequence SEQ ID NO: 7; or alternatively,
a VL of sequence SEQ ID NO: 8; or, alternatively,
a VH of sequence SEQ ID NO: 7 and a VL of sequence SEQ ID NO: 8.

In another embodiment of the second aspect of the invention, the antibody comprises a heavy chain consisting of a sequence that has at least 85%, at least 90%, or at least 95% sequence identity with SEQ ID NO: 9; and a light chain consisting of a sequence that has at least 85%, at least 90%, or at least 95% sequence identity with SEQ ID NO: 10. More particularly, the antibody comprises a heavy chain consisting of a sequence that has a sequence identity of 85%, 86%, 87%, 88%, 89%, 90%, 91%, 92%, 93%, 94%, 95%, 96%, 97%, 98% or 99% with SEQ ID NO: 9. Even more particularly, the heavy chain consists of a sequence SEQ ID NO: 9. More particularly, the light chain consists of a sequence that has a sequence identity of 85%, 86%, 87%, 88%, 89%, 90%, 91%, 92%, 93%, 94%, 95%, 96%, 97%, 98% or 99% with SEQ ID NO: 10. Even more particularly, the light chain consists of a sequence SEQ ID NO: 10.

In a particular embodiment of the first aspect of the invention, the antibody comprises a heavy chain consisting of sequence SEQ ID NO: 9 and a light chain consisting of sequence SEQ ID NO: 10.

Sequences SEQ ID NO: 1 to 10 are summarized in Table 1 below:

TABLE 1

| SEQ ID | Ab region | Amino acid sequence |
|---|---|---|
| SEQ ID NO: 1 | VH CDR3 | ARKGYRYDGYAMDY |
| SEQ ID NO: 2 | VL CDR3 | QQHYGSPLT |
| SEQ ID NO: 3 | VH CDR1 | GYSFTGYN |
| SEQ ID NO: 4 | VH CDR2 | IDTYYGGI |
| SEQ ID NO: 5 | VL CDR1 | QSLLNSNNQKNY |
| SEQ ID NO: 6 | VL CDR2 | FAS |
| SEQ ID NO: 7 | VH | EVQLQQSGPELAKPGASVKISCKASGYSFTGYNM NWVKQSNGKSLEWIGNIDTYYGGISYNQKFKDKA TLTVDKSSSTAYMQLKSLTSEDSAVYYCARKGYR YDGYAMDYWGQGTSVTVSS |
| SEQ ID NO: 8 | VL | DIVMTQSPSSLSMSVGQKVTMNCKSSQSLLNSNN QKNYLAWYQQKPGQSPKLLLYFASTRKSGVPDRF IGSGSGTDFTLTISSVQAEDLADYFCQQHYGSPL TFGAGTKLELK |
| SEQ ID NO: 9 | Heavy chain | MEWIWVFLFLLSGTAGVHSEVQLQQSGPELAKPG ASVKISCKASGYSFTGYNMNWVKQSNGKSLEWIG NIDTYYGGISYNQKFKDKATLTVDKSSSTAYMQL KSLTSEDSAVYYCARKGYRYDGYAMDYWGQGTSV TVSSSAKTTAPSVYPLAPVCGDTTGSSVTLGCLVK GYFPEPVTLTWNSGSLSSGVHTFPAVLQSDLYTL SSSVTVTSSTVVPSQSITCNVAHPASSTKVDKKI EPRGPTIKPCPPCKCPAPNLLGGPSVFIFPPKIK DVLMISLSPIVTCVVVDVSEDDPDVQISWFVNNV EVHTAQTQTHREDYNSTLRVVSALPIQHQDWMSG KEFKCKVNNKDLPAPIERTISKPKGSVRAPQVYV LPPPEEEMTKKQVTLTCMVTDFMPEDIYVEWTNN GKTELNYKNTEPVLDSDGSYFMYSKLRVEKKNWV ERNSYSCSVVHEGLHNHHTTKSFSRTPGK |
| SEQ ID NO: 10 | Light chain | MESQTQVLMFLLLVVVSGACADIVMTQSPSSLSM SVGQKVTMNCKSSQSLLNSNNQKNYLAWYQQKPG QSPKLLLYFASTRKSGVPDRFIGSGSGTDFTLTI SSVQAEDLADYFCQQHYGSPLTFGAGTKLELKRA DAAPTVSIFPPSSEQLTSGGASVVCFLNNFYPKD INVKWKIDGSERQNGVLNSWTDQDSKDSTYSMSS TLTLTKDEYERHNSYTCEATHKTSTSPIVKSFNR NEC |

As mentioned above, in a further aspect the invention also provides a conjugate comprising the antibody as defined in the first aspect.

All the embodiments related to the first aspect are also meant to apply to the conjugate of the invention.

The term "conjugate" as used herein refers to a compound that has been formed by the joining the antibody or the CD5L-binding fragment thereof of the first aspect with one or more compounds via either a covalent or non-covalent bond.

In a particular embodiment of this further aspect, optionally in combination with any of the embodiments provided above or below, the conjugate further comprises a diagnostic agent or a therapeutic agent.

In a more particular embodiment, optionally in combination with any of the embodiments provided above or below, the diagnostic agent is a label.

The word "label" when used herein refers to a detectable compound or composition which is conjugated directly or indirectly to the antibody so as to generate a "labelled" antibody. The label may be detectable by itself (e.g. radioisotope labels or fluorescent labels) or, in the case of an enzymatic label, may catalyze chemical alteration of a substrate compound or composition which is detectable.

The label may be directly, attached or may be attached via a linker (such as Adipic Acid Dihyrazide (ADH). The label may be attached by chemical conjugation. Methods of conjugating labels to antibodies are known in the art. For example, carbodiimide conjugation may be used to conjugate labels to antibodies. Other methods for conjugating a label to an antibody can also be used. For example, sodium periodate oxidation followed by reductive alkylation of appropriate reactants can be used, as can glutaraldehyde cross-linking.

In a particular embodiment of the further aspect, the therapeutic agent of the conjugate is a cytotoxic agent. In a more particular embodiment, the cytotoxic agent is selected from group consisting of a toxin, a drug moiety, and a nucleolytic enzyme. In an alternative embodiment, the cytotoxic agent is selected from group consisting of a chemotherapeutic agent, an antibiotic, and a radioactive isotope. In a particular embodiment, the conjugate further comprises a chemotherapeutic agent or a toxin.

Chemotherapeutic agents useful in the generation of such conjugates have been described in the state of the art. Enzymatically active toxins and fragments thereof that can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, *Phytolaca americana* proteins (PAPI, PAPn, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active asters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). In particular embodiments, a conjugate of the invention may comprise an antibody conjugated to one or more drug moieties through a linker.

In another embodiment of the further aspect of the invention, the conjugate further comprises a cell-penetrating agent. In a more particular embodiment, the cell-penetrating agent is a cell penetrating peptide. In a more particular embodiment, the cell-penetrating agent is a nanoparticle delivery system, which is known to be biocompatible and protect the antibody from degradation. In one embodiment, the nanoparticle delivery system is a lipidic nanoparticle. In another embodiment, the lipidic nanoparticle is selected from the group consisting of liposomes and solid-lipid nanoparticle. In another embodiment, the lipidic nanoparticle is a liposome.

The cell-penetrating agents can be further functionalized by conjugating molecules with the ability of recognizing and binding to molecules on Tcells or macrophages surface.

In a the third aspect of the invention, the antibody or fragment as defined in the first aspect of the invention, or alternatively, the conjugate as defined in the further aspect, is for use in cancer therapy, diagnosis or prognosis.

In a fourth aspect, the present invention provides a pharmaceutical composition comprising a therapeutically effective amount of a CD5L-binding agent together with one or more pharmaceutically acceptable carriers or excipients.

The term "CD5L-binding agent" includes any kind of molecule, either of protein or not protein kind with the ability of binding and blocking CD5L. That is, it is capable of binding CD5L and inhibiting its function. The CD5L-binding agent can be any anti-CD5L antibody or fragment thereof (either commercial or the one object of the first aspect of the invention), a peptide or small molecule. The ability of the agent to bind and block CD5L can be determined following the test provided above based on macrophage in vitro polarization. In one embodiment of the fourth aspect of the invention, the CD5L-binding agent is an anti-CD5L antibody or fragment thereof. In another embodiment of the fourth aspect of the invention, the CD5L-binding agent is a monoclonal antibody or fragment thereof. In another embodiment of the fourth aspect of the invention, the CD5L-binding agent is the monoclonal antibody or fragment thereof as defined in the first aspect of the invention.

The expression "therapeutically effective amount" as used herein, refers to the amount of the CD5L-binding agent that, when administered, is sufficient to prevent development of, or alleviate to some extent, one or more of the symptoms of the disease which is addressed. The particular dose of agent administered according to this invention will of course be determined by the particular circumstances surrounding the case, including the CD5L-binding agent administered, the route of administration, the particular condition being treated, and the similar considerations.

The expression "pharmaceutical composition" encompasses both compositions intended for human as well as for non-human animals (i.e. veterinarian compositions).

The expression "pharmaceutically acceptable carriers or excipients" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and non-human animals without excessive toxicity, irritation, allergic response, immunogenicity or other problems or complications commensurate with a reasonable benefit/risk ratio.

Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The relative amounts of the CD5L-binding agent, the pharmaceutically acceptable excipients, and/or any additional ingredients in a pharmaceutical composition of the invention will vary, depending upon the identity, size, and/or condition of the subject treated and further depending upon the route by which the composition is to be administered.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Excipients such as coloring agents, coating agents, sweetening, and flavouring agents can be present in the composition, according to the judgment of the formulator.

The pharmaceutical compositions containing the CD5L-binding agent of the invention can be presented in any dosage form, for example, solid or liquid, and can be administered by any suitable route, for example, oral, parenteral, rectal, topical, intranasal or sublingual route, for which they will include the pharmaceutically acceptable excipients necessary for the formulation of the desired dosage form, for example, topical formulations (ointment, creams, lipogel, hydrogel, etc.), eye drops, aerosol sprays, injectable solutions, osmotic pumps, etc.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, corn-starch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary binding excipients include, but are not limited to, starch (e.g., corn-starch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminium silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, ascorbyl stearate, ascorbyl oleate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

As described, the invention, in a fifth aspect, also provides a kit of parts comprising (a) a CD5L-binding agent or a pharmaceutical composition as defined in the fourth aspect of the invention; (b) a drug; and (c) optionally instructions for its use.

In a particular embodiment of the fifth aspect of the invention, optionally in combination with any of the embodiments above or below, the CD5L-binding agent is an anti-CD5L antibody or a CD5L-binding fragment thereof, or alternatively a conjugate comprising an anti-CD5L antibody or a CD5L-binding fragment thereof. In another embodiment of the fifth aspect of the invention, the CD5L-binding agent is an anti-CD5L antibody or CD5L-binding fragment thereof as defined in the first aspect of the invention, or alternatively, a conjugate as defined in a further aspect of the invention.

In another embodiment of the fifth aspect of the invention, optionally in combination with any of the embodiments provided above or below, the drug is an anticancer drug.

Another aspect of the invention provides a CD5L-binding agent, or an antibody or fragment thereof as defined in the first aspect, or a pharmaceutical composition as defined in the fourth aspect, or a kit as defined in the second or fifth aspect of the invention, for use in inhibiting macrophage M2 activation, or alternatively, for use in promoting lymphocyte T activation as illustrated in FIG. 6.

The term "macrophage M2 activation" refers to the phenotypic changes that macrophages undergo when exposed to a molecule or a group of molecules that induce a macrophage anti-inflammatory, pro-regenerative and tolerant phenotype. Herein, M2 activated macrophages are generally obtained by treating macrophages either with IL10 or cancer cells conditioned media (CM). The terms "macrophage M2 activation" and "macrophage M2 polarization" mean the same and are interchangeable. The term "M2 macrophage" is used interchangeable with "M2 type macrophage" or "M2 type activated macrophage" in the present invention.

Several tests can be followed to determine the inhibition of macrophage M2 activation. For example, by in vitro polarization tests of macrophages as described in the examples below. Briefly, the agent to be tested is added along with an M2-inducer cytokine, such as IL10 (although any other can be used instead) to a culture of macrophage-like cells, such as PB monocytes, THP1 cells, U937 cells, or K562 cells, and then the mRNA expression levels of one or more of the macrophage activation markers VEGF, CD163, and Mertk are measured. The skilled person can design appropriate primers to determine the level of expression. Illustrative non-limitative examples of such primers are sequences SEQ ID NO: 17 to 20 and 25 to 26.

As detailed above, a seventh aspect of the invention provides a CD5L-binding agent, or an antibody or fragment thereof as defined in the first aspect, or a conjugate as defined in a further aspect, or a pharmaceutical composition as defined in the fourth aspect, or a kit as defined in the second or fifth aspect for use in the treatment and/or prevention of cancer. In a particular embodiment, the treatment and/or prevention of cancer is through the inhibition of macrophage M2 activation, or alternatively, through the promotion of lymphocyte T activation.

As it has been discussed above, the inhibition of M2 activation and the promotion of lymphocyte T activation has direct applications in the treatment of cancer. It has been reported in the prior art that the macrophage M2 activation leads to immune tolerance towards tumors (Mantovani A. et al., supra). The fact that a CD5L-binding agent is capable of inhibiting the immunosuppressive state of macrophages (i.e. M2 activation), means that it can be used to reprogram the immune system in order to eliminate tumoral cells. And, consequently, this can have a beneficial effect in the treatment of cancer.

The term "cancer" generically refers to any neoplastic disease. Illustrative non-limiting examples of cancer which can be treated with the CD5L-binding agent or pharmaceutical composition of the invention include, although they are not limited to, papillomas, adenomas, lipomas, osteomas, myomas, angiomas, nevi, mature teratomas, carcinomas, sarcomas, immature teratomas, melanoma, myeloma, leukemia, Hodgkin's lymphoma, basalioma, spinalioma, breast cancer, ovarian cancer, uterine cancer, lung cancer, bronchial cancer, prostate cancer, colon cancer, pancreatic cancer, kidney cancer, esophageal cancer, hepatocellular carcinoma (HCC), head and neck cancer, etc.

As detailed above, another aspect of the invention provides a CD5L-binding agent, or an antibody or fragment thereof as defined in the first aspect, or a conjugate as defined in a further aspect, or a pharmaceutical composition as defined in the fourth aspect, or a kit as defined in the second or fifth aspect for use in combination therapy with an anticancer agent in the treatment and/or prevention of cancer. Particularly, the CD5L-binding agent, or the antibody or fragment thereof, or the pharmaceutical composition is administered simultaneously, sequentially or separately with an anticancer agent, or a derivative thereof. More particularly, they are administered separately, in any order, within a therapeutically effective interval.

In a ninth aspect the present invention provides a diagnostic or prognostic method based on determining CD5L in macrophages.

"Diagnosis" as used herein has to be understood as becoming aware of a particular medical condition, syndrome, complication or risk in a subject; the determination of the nature of the disease or condition; or the distinguishing of one disease or condition from another. It refers both to the process of attempting to determine or identify the possible disease or disorder, and to the opinion reached by this process. A diagnosis, in the sense of diagnostic procedure, can be regarded as an attempt at classification of an individual's condition into separate and distinct categories that allow medical decisions about treatment and prognosis to be made. Subsequently, a diagnostic opinion is often described in terms of a disease or other condition. However, a diagnosis can take many forms. It might be a matter of detecting the presence and naming the disease, lesion, dysfunction or disability. It might be an exercise to attribute a category for management or for prognosis. It may indicate either degree of abnormality on a continuum or kind of abnormality in a classification.

"Prognosis" as used herein refers to the prediction of the probable progression and outcome of a disease. It includes: neoplasm grading (attempt to express in replicable terms the level of cell differentiation in neoplasms as increasing anaplasia correlates with the aggressiveness of the neoplasm), neoplasm staging (attempt to express in replicable terms the extent of the neoplasm in the patient).

As used herein, the expression "CD5L in macrophages" refers to the CD5L protein located at macrophages, independently of whether it is located inside or on the surface of the cells.

In one embodiment of the ninth aspect of the invention, when the amount of CD5L in macrophages is higher than a reference value is indicative of bad prognosis.

In the present invention, unless otherwise stated, the term "reference value" is to be understood as a predefined value of CD5L in macrophages in the present case, which is derived from the levels of said molecular marker in a sample or group of samples. The samples are taken from a subject or group of subjects wherein the presence, absence, stage, or course of the disease has been properly performed previously. This value is used as a threshold to determine the prognosis of the disease, among others. This reference value is also useful for determining whether the subject has to initiate a medical regimen and how effective the regimen is. The subject or subjects from whom the "reference value" is derived may include subject/s wherein the condition is absent, subject/s wherein the condition is present, or both. The skilled person in the art, making use of the general knowledge, is able to choose the subject or group of subjects more adequate for obtaining the reference value for each of the methods of the present invention.

Methods for obtaining the reference value from the group of subjects selected are well-known in the state of the art (Burtis C. A. et al., 2008, Chapter 14, section "Statistical Treatment of Reference Values"). In a particular case "reference value" is a cut-off value defined by means of a conventional ROC analysis (Receiver Operating Characteristic analysis). As the skill person will appreciate, optimal cut-off value will be defined according to the particular applications of the prognostic method: purpose, target population for the, balance between specificity and sensibility, etc.

In another embodiment of the ninth aspect of the invention, the amount of CD5L in macrophages is determined by an immunoassay technique. In another embodiment of the ninth aspect of the invention, the immunoassay technique is immunohistofluorescence, immunohistochemistry, or flow cytometry.

In another embodiment of the ninth aspect of the invention, the bad prognosis is the risk of mortality.

In another embodiment of the ninth aspect of the invention, the risk of mortality proportionally increases with the amount of CD5L on tumor macrophages.

In an embodiment of the ninth or the tenth aspect of the invention, the macrophages are TAMs.

As mentioned above, in a tenth aspect the invention provides the use of CD5L as a diagnostic or prognostic marker of cancer, or as a marker for monitoring cancer, in an isolated macrophage-comprising biological sample.

The term "isolated macrophage-comprising biological sample" encompasses samples that contain macrophages and other things, and samples where macrophages have been isolated for their further analysis.

In an eleventh aspect the present invention provides means for the diagnostic or prognostic method based on the determination of the amount of CD5L in macrophages. In one embodiment, the macrophages are TAMs.

The term "means" refers to any reactants or apparatus useful in the determination of protein amounts. For example, the means may be an antibody or an ELISA kit, among others.

In one embodiment of the eleventh aspect of the invention, the means is an antibody or a CD5L-binding fragment thereof which specifically binds to CD5L. In one embodiment, the macrophages are TAMs. In another embodiment of the eleventh aspect of the invention, the antibody is as defined in the first aspect of the invention. In another embodiment of the eleventh aspect of the invention, the antibody forms part of a kit.

In a twelfth aspect the present invention provides a companion diagnostic method for determining the efficacy of a medical regimen.

As used herein, "companion diagnostic methods" are assays used to identify subjects susceptible to treatment with a particular treatment or to monitor treatment and/or to identify an effective dosage for a subject or sub-group or other group of subjects. Companion diagnostics may be useful for stratifying patient disease, disorder or condition severity levels, allowing for modulation of treatment regimen and dose to reduce costs, shorten the duration of clinical trial, increase safety and/or increase effectiveness. Companion diagnostics may be used to predict the development of a disease, disorder or condition and aid in the prescription of preventative therapies. Some companion diagnostics may be used to select subjects for one or more clinical trials. In some cases, companion diagnostic assays may go hand-in-hand with a specific treatment to facilitate treatment optimization. In a particular embodiment, the treatment of the companion diagnostic method is an anticancer treatment. In a more particular embodiment, the treatment of the companion diagnostic method is carried out with an antibody, a conjugate, or a pharmaceutical composition of the invention.

In the present invention, the expression "medical regimen" is to be understood as encompassing either pharmacological therapies (such as chemotherapy and radiotherapy) as well as other clinical decisions taken by a physician (such as surgery in order to extirpate the part of the tissue affected by the disease), among others.

In one embodiment of the twelfth aspect of the invention, the method further comprises the step (b) comparing the amount obtained in step (a) with a reference value, wherein if the amount of CD5L in macrophages detected in step (a) is higher than the reference value it is indicative that the subject would benefit from the medical regimen.

In one embodiment of the twelfth and thirteenth aspects of the invention, the means is an antibody or a CD5L-binding fragment thereof which specifically binds to CD5L. In one embodiment, the macrophages are TAMs. In another embodiment of the twelfth and thirteenth aspects of the invention, the antibody is as defined in the first aspect of the invention. In one embodiment of the twelfth and thirteenth aspects of the invention, the antibody forms part of a kit.

In one embodiment of the ninth, eleventh, twelfth, or thirteenth aspects of the invention, optionally in combination with any embodiment above or below, the biological sample is selected from the group consisting of tissue and peripheral blood. In another embodiment the biological sample is a tumor tissue sample.

The term "biological sample" embraces both the sample directly obtained from the subject as well as in the form of a cell culture.

In a fourteenth aspect, the present invention provides an in vitro method for determining the presence of M2 macrophages in an isolated sample from a subject, the method comprising the step of determining the amount of CD5L in macrophages from the sample.

In one embodiment of the fourteenth aspect of the invention, the CD5L is localized on the surface of the macrophages.

In one embodiment of the fourteenth aspect of the invention, the step of determining the amount of CD5L is performed by an immunoassay technique. In another embodiment of the fourteenth aspect of the invention, the immunoassay technique is immunofluorescence, immunochemistry, or flow cytometry. In another embodiment of the fourteenth aspect of the invention, the immunoassay technique is carried out using an anti-CD5L antibody. In another embodiment of the fourteenth aspect of the invention, the anti-CD5L antibody is as defined in the first aspect of the invention. In another embodiment of fourteenth aspect of the invention, the anti-CD5L antibody forms part of a kit.

In one embodiment of the fourteenth aspect of the invention, the method comprises a step previous to the determination of the amount of CD5L, wherein the macrophage fraction is isolated from the biological sample.

Macrophages can be identified and/or isolated from biological samples following routinary techniques in the field of immunology. The skill in the art can adjust the parameters of the techniques for optimal results. For illustrative purposes, antibodies against the surface protein CD14 could be used to identify and isolate the macrophage population of a biological sample by Flow Cytometry techniques. Alternatively, antibodies against the surface protein CD68 can be used to identify the macrophages of a biological sample by immunochemistry or immunofluorescence techniques.

In one embodiment of the fourteenth aspect of the invention, when the amount of CD5L in macrophages is higher than a reference value is indicative of the presence of M2. The term "reference value" referred in this embodiment of the fourteenth aspect of the invention, is to be understood as a predefined value of CD5L in inactivated macrophages (i.e. in M0 phase).

In a fifteenth aspect, the present invention provides the use of CD5L as a marker of M2 macrophage.

The invention also provides an anticancer compound for use in a method of treatment of a patient with cancer, wherein the method comprises (i) determining the amount of CD5L in macrophages from a test sample from the patient; and (ii) if the amount of CD5L in macrophages of the test sample is higher than a reference value, administering to the patient an effective amount of an anticancer drug. In a particular embodiment, the anticancer drug is a known anticancer drug. In a more particular embodiment, the anticancer drug is the antibody, the conjugate or the pharmaceutical composition of the invention.

As used herein, an "anticancer compound" refers to any compound that stops or inhibits cancer development or progression. Furthermore, said compound may work on the inhibition or arrest of cell proliferation, or on the survival of proliferating cells, but may also have an effect on other cellular activities.

The invention also provides a method for treating cancer in a subject, wherein the method comprises (i) determining the amount of CD5L in macrophages from a test sample from the patient; and (ii) if the amount of CD5L in macrophages from the test sample is higher than a reference value, administering to the patient an effective amount of an anticancer drug together with pharmaceutical excipients or carriers. In a particular embodiment, the anticancer drug is a known anticancer drug. In a more particular embodiment, the anticancer drug is the antibody, the conjugate or the pharmaceutical composition of the invention.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Example 1

Materials and Methods
Production of Recombinant Human CD5L (rhCD5L)

The cDNA of human CD5L was obtained by gene synthesis (GenScript Piscataway, N.J., USA) following NCBI reference sequence NP_005885 (version NP_005885.1), with a modification in which the Immunoglobulin g chain signal peptide replaced that of hCD5L. The cDNA was cloned into the p.evi vector and transiently transfected into CHO K1 cells using the eviFect system (Evitria AG, Switzerland). Cells were grown in eviMake®, a chemically defined, serum-free, animal component-free medium. The cell culture supernatant was harvested at day 8 after transfection, dialyzed to 20 mM $Na_2HPO_4$, pH 7.4 and subjected to MonoQ chromatography. Recombinant hCD5L (rhCD5L) was eluted in a sodium chloride gradient, and purification was monitored by SDS-PAGE. Purified protein was dialyzed to PBS, concentrated by centrifugation on Amicon ultra (Millipore, UFC901024), and possible endotoxin contamination was removed by Endotrap columns (Hyglos GmbH, 321063), following the manufacturer's protocol. The purified rhCD5L was tested in preliminary experiments, where its activity in terms of macrophage (Mφ) TNFα secretion, as well as inhibition of apoptosis induced by cycloheximide treatment, was comparable to that of commercially available rhCD5L (R&D Systems) (data not shown).

Animals

Animal maintenance followed European Union and national guidelines for animal experimentation and treatment protocols were approved by the CNB/CSIC Ethics Committee for Animal Research. Research was approved by the CNB/CBMSO/CSIC Ethics Committee for Joint Research, and the ethical committee from Parc Cientffic de Barcelona and Universitat de Barcelona.

Generation of a Monoclonal Anti-CD5L Antibody of the Invention (4D7)

Murine mAbs against human CD5L were raised by subcutaneous immunization of BALB/c mice with 25 μg of a KLH-coupled rCD5L. Coupling to KLH was performed to increase immunogenicity, using maleimide-activated KLH, following standard procedures as recommended in SIGMA (Maleimide Activated BSA, KLH Conjugation Kit, MO, USA). 25 μg of KLH-coupled to 0.15 mL of sterile PBS emulsified with the same volume of Freund's complete adjuvant (Difco). Mice were boosted subcutaneously on days 28 and 56 with the same amount of protein in Freund's incomplete adjuvant.

Serum from immunized mice was collected 10 days after the last boost, and the presence of specific antibodies against rCD5L was determined in enzyme-linked immunosorbent assay (ELISA). Briefly, 500 ng rCD5L were immobilized in the wells of an ELISA plate (Nunc, Denmark) overnight at 4° C. Plates were blocked with PBS containing 5% BSA (SIGMA) for 1 h at 22° C. Then, serum was added at a 1:1, 1:5, 1:10 dilution in blocking buffer, and incubated for 1 h at 22° C. Between each step, the plates were washed twice with PBS 0.01% Tween-20 to remove unbound proteins. For bound antibody detection, a 1:1000 dilution of peroxidase (PO)-labeled antimouse IgG antibody (SIGMA) was added at the final step and incubated for 30 min at 22° C. Unbound antibody was washed three times with PBS 0.01% Tween-20. Color was developed by adding 3,30,5,50-tetramethylbenzidine liquid substrate (Sigma), and the optical density was read at 405 nm.

Selected mice were boosted intravenously with 30 μg of KLH-conjugated protein in sterile PBS three days before fusion of spleen lymphocytes with the P3X63Ag8.653 murine plasmacytoma (CRL1580, American Type Culture Collection) using polyethylene glycol 4000 (Merck). Cell fusion was performed using standard procedures (see Galfre G. et al., "Antibodies to major histocompatibility antigens produced by hybrid cell lines". Nature. 1977; 266:550-552. and Harlow E. and Lane D. E., "Antibodies: A Laboratory Manual". Cold Spring Harbor, New York: Cold Spring Harbor Laboratory Press, 1988. Two weeks after fusion, culture supernatants were screened in ELISA as indicated above for the presence of CD5L-specific antibodies using bovine serum albumin as negative control.

Positive hybridomas were cloned by limiting dilution following standard procedures (see Galfre G. et al. and Harlow E. et al., supra). mAbs were synthesized in tissue culture supernatants and purified by affinity chromatography using Protein G-Sepharose (GE Healthcare). The immunoglobulin subclass was determined by ELISA using specific peroxidase-conjugated antibodies against the heavy chain of mouse immunoglobulins (IgG1, IgG2a, IgG2b, IgG3 and IgM) using the Rapid ELISA mouse mAb Isotyping kit (Thermo Fisher-Pierce) following the manufacturer's instructions.

It was concluded that mAb used in the present application was of subclass IgG2a.

Sequencing of 4D7 Anti-CD5L Antibody and Sequence Analysis

The anti-CD5L monoclonal antibody was sequenced from mRNA extracted from the 4D7 producing hybridoma cell line using the RNeasy mini kit (Qiagen, Germany), following the manufacturer's instructions. Then, mRNA was reverse transcribed to cDNA, with RNA to cDNA ecodry kit (Takara, Japan), following the manufacturer's instructions. The cDNA was used to PCR amplifications using the primers listed on Table 2. Amplified cDNA was resolved in agarose gels, excised from the gel and purified using Qiaquick PCR purification kit (Qiagen), and sequenced with the same primers by SANGER sequencing, using the BigDye™ Terminator v3.1 Cycle Sequencing Kit (Thermofisher, MS, USA), and the IGTP Genomics platform services. Primers used for RT-PCR and sequencing are listed in Table 2:

TABLE 2

| Gene | Nucleotide sequence | SEQ ID |
|---|---|---|
| Heavy chain Variable Fw1 | CAGTGGATAGACAGATGGGG | SEQ ID NO: 27 |
| Heavy chain Variable RV1 | GGGAATTCGAGGTGCAGCTG CAGGAGTCTGG | SEQ ID NO: 28 |
| Heavy chain Variable Fw2 | CTGGGTCTTTCTCTTCCTC CTG | SEQ ID NO: 29 |
| Heavy chain Variable RV2 | CGTACCTATAGCCCTTTCT TGC | SEQ ID NO: 30 |
| Light chain Variable Fw1 | GGGAATTCACTGGATGGTGG GAAGATGG | SEQ ID NO: 31 |
| Light chain Variable RV1* | GGGAGCTCGAYATTGTGMTS ACMCARWCTMCA | SEQ ID NO: 32 |
| Light chain Variable Fw2 | GAATCACAGACCCAGGTC CTC | SEQ ID NO: 33 |
| Light chain Variable RV2 | ACGTGAGCGGAGAGCCATAA | SEQ ID NO: 34 |

*Y = C or T; M = A or C; S = C or G; R = A or G; W = A or T.

The analysis of the sequence and the identification of the different regions and domains were performed through the use of the NCBI Basic Local Alignment Search Tool (BLAST, NCBI; USA) and the IMGT®, international ImMunoGeneTics information System® http://www.imgt.org, CNRS, France.

Thus, it was found that 4D7 antibody comprises a heavy chain of sequence SEQ ID NO: 9 and a light chain of sequence SEQ ID NO: 10.

Primary Cells and Cell Lines

Buffy coats, provided by the Blood and Tissue Bank (Barcelona, Spain), were obtained from healthy blood donors following the institutional standard operating procedures for blood donation and processing.

For monocyte isolation, CD3+ cells were depleted by RosetteSep human CD3 depletion cocktail (StemCell Technologies, 15621, Vancouver, BC, Canada). Peripheral blood mononuclear cells (PBMCs) were isolated as previously described (Sanjurjo L, et al., The human CD5L/AIM-CD36 axis: A novel autophagy inducer in macrophages that modulates inflammatory responses. Autophagy. Taylor and Francis Inc.; 2015; 11(3):487-502) by Ficoll-Paque (GE Healthcare, 17-1440, Piscataway, N.J., USA) density gradient centrifugation at 400 g for 25 min. CD3+ T cells were isolated from the PBMCs by negative selection using MagniSort Human T cell enrichment Antibodies cocktail and MagniSort negative selection beads (Invitrogen by Thermo Fisher Scientific,), following the manufacturer's instructions. Recovered cells were washed twice in PBS and counted using Perfect-Count microspheres (Cytognos, CYT-PCM, Salamanca, Spain), following the manufacturer's instructions. The cells were counted using Perfect-Count microspheres. $2 \times 10^6$ or $2 \times 10^5$ PBMCs per well were seeded in 6-well plates (Nunc, Denmark) or Millicell EZ slides (Merck Millipore, PEZGS0816, Billerica, Mass., USA) respectively, and peripheral blood monocytes (PB monocytes) were isolated by adherence in a 5% CO2 incubator at 37° C. for 30 min. Non-adherent cells were removed and the adherent cells were washed twice with PBS and incubated in RPMI 10% FBS (Lonza, DE14-840E, Basel, Switzerland), 100 U/mL penicillin and 100 μg/mL streptomycin (Sigma-Aldrich, P0781, St. Louis, Mo., USA) for 24 h prior the experiments. Percentage of adherent cells CD14+ (PB monocytes) routinely obtained were 94.98% (+/−3.26%), and that of CD3+ T cells was always greater than 90%. Cell viability was routinely >94%.

The Lewis Lung Carcinoma (LLC) cell line 3LLR was cultured in Dulbecco's modified eagle medium (DMEM, GIBCO, Invitrogen, NY), supplemented with penicillin (100 U/ml), streptomycin (100 μg/ml) and 10% FBS.

Liver Cancer Cell Conditioned Medium

HepG2, Huh7 and SNU398 cells were purchased from ATCC (The American Type Culture Collection), and cultured in EMEM (HepG2), DMEM (Huh7) or RPMI (SNU398) supplemented with 2 mM glutamine (Lonza, Basel, Switzerland), 100 U/mL penicillin and streptomycin (Sigma-Aldrich) and 10% heat-inactivated fetal bovine serum (FBS) (Lonza).

Cells were grown to 90% confluency, then washed with PBS, and medium was replaced with RPMI containing 2% FBS. Twenty-four hours later, the supernatant was collected and centrifuged at 10,000 rpm for 10 min at 4° C. to remove cellular debris.

In Vitro Polarization of Macrophages

PB monocytes were polarized by adding into the culture medium INF (interferon)/LPS (lipopolysaccharide), IL4 (interleukin 4), IL10 (interleukin 10), DXM (dexamethasone) or liver cancer cell CM (conditioned medium) as follows:
- INF/LPS: 50 ng/mL IFNγ (Preprotech, 300-02-A, Rocky Hill, N.J., USA) plus 100 ng/mL LPS from E. coli 011134 (Sigma-Aldrich; 14391);
- IL4, 40 ng/ml IL-4 (Preprotech; 200-04-A);
- IL10, 50 ng/ml IL-10 (Preprotech; 200-10-A);
- DXM, 40 ng/ml Dexamethasone (Kern pharma, 672066.0, Terrasa, Spain);
- CM, a pool of conditioned media collected from Huh7, HepG2, or SNU-398 cells (see above).

The control population of PB monocytes, cultured without polarizing cytokines is referred to as M or medium.

To assess the effect of recombinant human CD5L (rhCD5L, produced as above described) on PB monocytes, these cells were incubated for 24 h in culture medium as above described with 1 μg/ml albumin purified from human plasma, used as control protein (Grifols, 670612.1, Barcelona, Spain), or 1 μg/ml endotoxin-free rhCD5L.

To assess the role of 4D7 antibody on IL-10 induced polarization, this antibody or an IgG2a isotype control antibody (R&D systems, Minneapolis, Minn., USA), was added at a final concentration of 5 μg/ml (for real time PCR, explained below), 45 mins prior to IL-10 addition to the culture.

Macrophage Stimulation with LPS 50.000 inactivated or IL10 activated PB macrophages were stimulated with 10 ng/ml LPS (from E. coli 0111:B4, Invivogen, San Diego, Calif., USA) for 4 h. Then, cytokines in the supernatant were measured by ELISA with the OptEIA ELISA (BD Biosciences) following the manufacturer's instructions. Color was developed by adding 3,3',5,5'-tetramethylbenzidine liquid substrate (Sigma-Aldrich, T8665), and the optical density was read at 450 nm on a Varioskan Flash microplate reader (Thermo Fisher Scientific Inc.).

Flow Cytometry Analyses of Macrophage Polarization Markers

Polarized macrophages were detached with Accutase (Sigma-Aldrich), washed twice in PBS, and incubated with 50 μl of PBS containing 10% human AB serum, 2% FBS, and 0.02% $NaN_3$ (blocking buffer) for 30 min on ice.

Cells were then incubated with a combination of fluorescently conjugated anti-human CD163 monoclonal antibodies (from BD Biosciences 563889) for 20 min in Brilliant stain buffer (BD Biosciences, 563794). They were then rinsed with washing buffer (PBS containing 2% FBS and 0.02% $NaN_3$) and fixed with 1% paraformaldehyde.

Flow cytometric analysis was performed on a BD LSR Fortessa instrument and using FACSDiva software (BD Biosciences), following manufacturer's instructions, with 10,000 events acquired for each sample.

RNA Extraction and Quantitative RT-PCR

PB monocytes ($1 \times 10^6$ cells/well) were incubated for 24 h in RPMI medium containing 5% FCS and the polarizing stimuli described above or the LXR agonist T1317 (Tocris Bioscience, Bristol, UK), plus 9-cis-retinoic acid (9cRa) (Sigma-Aldrich) (T13+9CR), 1 μM used as a positive control of CD5L mRNA induction.

Cells were then washed with PBS and disrupted with QIAzol Lysis Reagent (Qiagen, 79306, Hilden, Germany), and total RNA was extracted using the miRNeasy Mini Kit (Qiagen, 217004).

Total RNA (1 μg) was reverse transcribed using the RNA to cDNA EcoDry™ Premix (Clontech, 639549, Mountain View, Calif., USA). Each RT-PCR reaction was then amplified in a LightCycler® 480 PCR system using the KAPA SYBR Fast Master Mix (KAPA Biosystems, 51230-100, Woburn, Mass., USA). Samples were incubated for an initial denaturation at 95° C. for 5 min, then 40 PCR cycles were performed using the following conditions: 95° C. for 10 s, 60° C. for 20 s and 72° C. for 10 s. All primer pairs used in this study are listed in Table 3.

TABLE 3

| Gene | Nucleotide sequence | SEQ ID |
|---|---|---|
| CD80 forward | CTGCCTGACCTACTGCTTTG | SEQ ID NO: 11 |
| CD80 reverse | GGCGTACACTTTCCCTTCTC | SEQ ID NO: 12 |
| TNFα forward | GAGGAGGCGCTCCCCAAGAAG | SEQ ID NO: 13 |
| TNFα reverse | GTGAGGAGCACATGGGTGGAG | SEQ ID NO: 14 |
| TGM2 forward | CCTCGTGGAGCCAGTTATCAA | SEQ ID NO: 15 |
| TGM2 reverse | GTCTGGGATCTCCACCGTCTTC | SEQ ID NO: 16 |

TABLE 3-continued

| Gene | Nucleotide sequence | SEQ ID |
|---|---|---|
| CD163 forward | CACCAGTTCTCTTGGAGGAACA | SEQ ID NO: 17 |
| CD163 reverse | TTTCACTTCCACTCTCCCGC | SEQ ID NO: 18 |
| MERTK forward | CTCTGGCGTAGAGCTATCACT | SEQ ID NO: 19 |
| MERTK reverse | AGGCTGGGTTGGTGAAAACA | SEQ ID NO: 20 |
| GAPDH forward | TCTTCTTTTGCGTCGCCAG | SEQ ID NO: 21 |
| GAPDH reverse | AGCCCCAGCCTTCTCCA | SEQ ID NO: 22 |
| Cd5l forward | AGCTCATCACCTTCACCTGC | SEQ ID NO: 23 |
| Cd5l reverse | CCCAGAGCAGAGGTTGTCTC | SEQ ID NO: 24 |
| Vegf forward | AGGGCAGAATCATCACGAAGT | SEQ ID NO: 25 |
| Vegf reverse | AGGGTCTCGATTGGATGGCA | SEQ ID NO: 26 |

Gene expression values were normalized to the expression levels of GAPDH (glyceraldehyde 3-phosphate dehydrogenase). Fold induction levels were calculated by using as a reference the levels of expression of each gene in cells untreated (−).

CD5L Cell Surface Expression Analysis by Flow Cytometry $2 \times 10^5$ PB monocytes in the culture medium above indicated or polarized with the stimuli indicated in the figures for 72 h were detached with accutase (Sigma-Aldrich, A6964), washed twice in ice-cold PBS, and incubated with 100 µl of blocking buffer, PBS containing 10% FCS (Lonza) and 10% human AB serum (Sigma-Aldrich, H4522) for 30 min on ice.

Cells were then incubated with mAb anti-CD5L (C18, Abnova, H00000922-M01; or 4D7) for 60 min at 4° C. in blocking buffer. Cells were washed once with 3 ml PBS containing 2% FCS and 0.02% $NaN_3$ (washing buffer), and incubated, with fluorescein isothiocyanate-conjugated anti-mouse IgG/IgM antibody (BD) or Alexa Fluor® 647 F(ab')2 fragment of goat anti-rabbit IgG (Molecular Probes, Thermo Fisher Scientific, A-21246) in blocking buffer for 45 min at 4° C. After washing cells with 3 ml washing buffer, flow cytometric analysis was performed on a FACSCantoII instrument (BD) and using FACSDiva software (BD) according to manufacturer's instructions.

Immunofluorescence (IF) Analysis of HCC Tissue Microarrays

All human studies were conducted following the Declaration of Helsinki principles and current legislation on the confidentiality of personal data and were approved by the Human Ethics Committee of the Hospital Universitari Germans Trias i Pujol. Retrospective samples from HCC patients were obtained from various Spanish hospitals: Josep Trueta, HuGTiP, Mar, Universitario Central de Asturias and Parc Taulí Consortium. After an exhaustive pathological inspection, the most representative areas of the tumors or adjacent tissue were chosen to build tissue microarrays (TMAs).

Briefly, tissue cylinders of 0.6 mm in diameter from these areas were included in a paraffin block with an area spanning 0.7-0.8 mm. Next, 5 µm sections were mounted on silanized glass slides (Dako, Barcelona, Spain) in duplicates or triplicates depending on tissue heterogeneity.

In addition, amygdala, colon, and fetal liver were included in the TMAs as internal controls.

Immunofluorescence (IF) was performed on TMA sections using the VENTANA Benchmark IHC platform (Ventana Medical Systems, Tucson, Ariz., USA).

Antibodies against hCD5L (4D7), and CD68 (Sigma) at a working dilution of 1:100 were used. Depending on the primary antibody, anti-mouse or -rabbit IgG coupled with Alexa-488 or Alexa-647 (Invitrogen) were used as a secondary antibody.

Finally, nuclei were stained with PBS containing 800 nM DAPI (Sigma-Aldrich) for 10 min at room temperature.

Secondary antibodies alone were used for background immunofluorescence analysis.

Confocal microscopy images were taken with a FluoView™ FV1000 Spectral Confocal microscope and analyzed with FluoView™ FV10-ASW 3.1 software (Olympus, Shinjuku, Tokyo, Japan).

In Vivo Assay of Immunotherapy

Wild-type C57BL/6, were injected with 3×106 3LLR cells subcutaneously in the flanks. Tumors were allowed to grow for 7 days, and then, 150 µg of CD5L moAb D7 in PBS was given intraperitoneally (i.p.) or an equal volume of PBS as control (n=5 mice/group), every three days for 7 days. Tumor size were measured manually with a caliper every day since day 7, and tumor volume was calculated by $(v=\pi \times [w^2 \times l]/6)$ (width, w and length, l). Mice were sacrificed at day 15 and tumors and spleens were collected for further analyses.

T Cell Proliferation Assay

CD3+ T cells were stained with CellTrace Violet cell proliferation kit (Invitrogen) following the manufacturer instructions. Cells were allowed to rest overnight and then stimulated with CD2/3/28-coated beads at 1:10 ratio (bead/T cell) using the T cell activation/expansion kit (Miltenyi Biotech) in the presence/absence of 1 µg/ml rhCD5L, for 5 days at 37 C 5% of CO2. T cell proliferation was measured after 5 days in a LSR Fortessa Analyzer (BD Biosciences) and expressed as the percentage of FSChighVioletlow cells out of the living cells gated by FSC/SSC using the proliferation module of the FlowJo V9.8.2.

Statistical Analysis

Statistical analysis was performed with GraphPad Prism V.5 software (La Jolla, Calif., USA). Specific statistical tests are indicated in each figure legend. For survival analysis, Kaplan-Meier's method and log rank test were performed to compare differences among curves. Values of $*p \leq 0.05$ were considered significant.

Results

M2 Activated Macrophages Express CD5L

The inventors tested whether in vitro M2 polarization of macrophages induced any changes on CD5L expression.

Peripheral blood (PB) monocytes were polarized with Interferon (IFN), Lipopolysaccharide (LPS), IFN/LPS, interleukin 4 (IL4), and interleukin 10 (IL10), dexamethasone (Dexa) or with liver cancer cell conditioned medium control (CM ct), conditioned medium from Huh7 cells (CM Huh7), from HepG2 cells (CM HepG2), or from SNU cells (CM SNU). As positive control, Nuclear Receptor ligands T13+9cR or recombinant CD5L were used. As negative control, normal medium (M) or human albumin (hSA) were used. Then, CD5L mRNA (FIG. 1 A) and protein levels (FIG. 1 B) were studied by real time PCR, IF and flow cytometry.

The results showed that very low levels of CD5L mRNA (FIG. 1 A) and CD5L protein (FIG. 1 B) were detected in unstimulated (M), IFN, LPS or IL4-treated macrophages.

Figure 1:
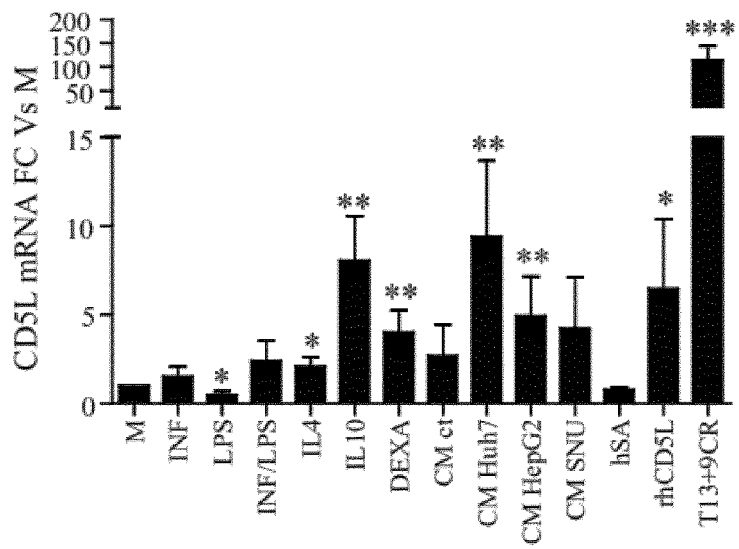
FIG. 1 shows the expression of CD5L and CD163 in peripheral blood (PB) monocytes polarized with various stimuli. (A) shows a bar diagram representing the levels of CD5L mRNA analyzed by real time PCR in PB monocytes after the application of the treatments indicated. The y-axis represents the fold change increase of CD5L mRNA levels after each treatment in comparison to control cells (M). *$p<0.001$, t-test vs M. (B) shows the surface levels of the proteins CD5L and CD163 analyzed by flow cytometry in PB monocytes after applying the stimuli indicated. The y-axis either represents the percentage of positive cells for each marker (panels above), or the mean fluorescence intensity (MFI) of each marker (panels below). * $p<0.001$, **$p<0.01$ ANOVA test with Bonferroni post test, IL10 vs all.
Figure 1:
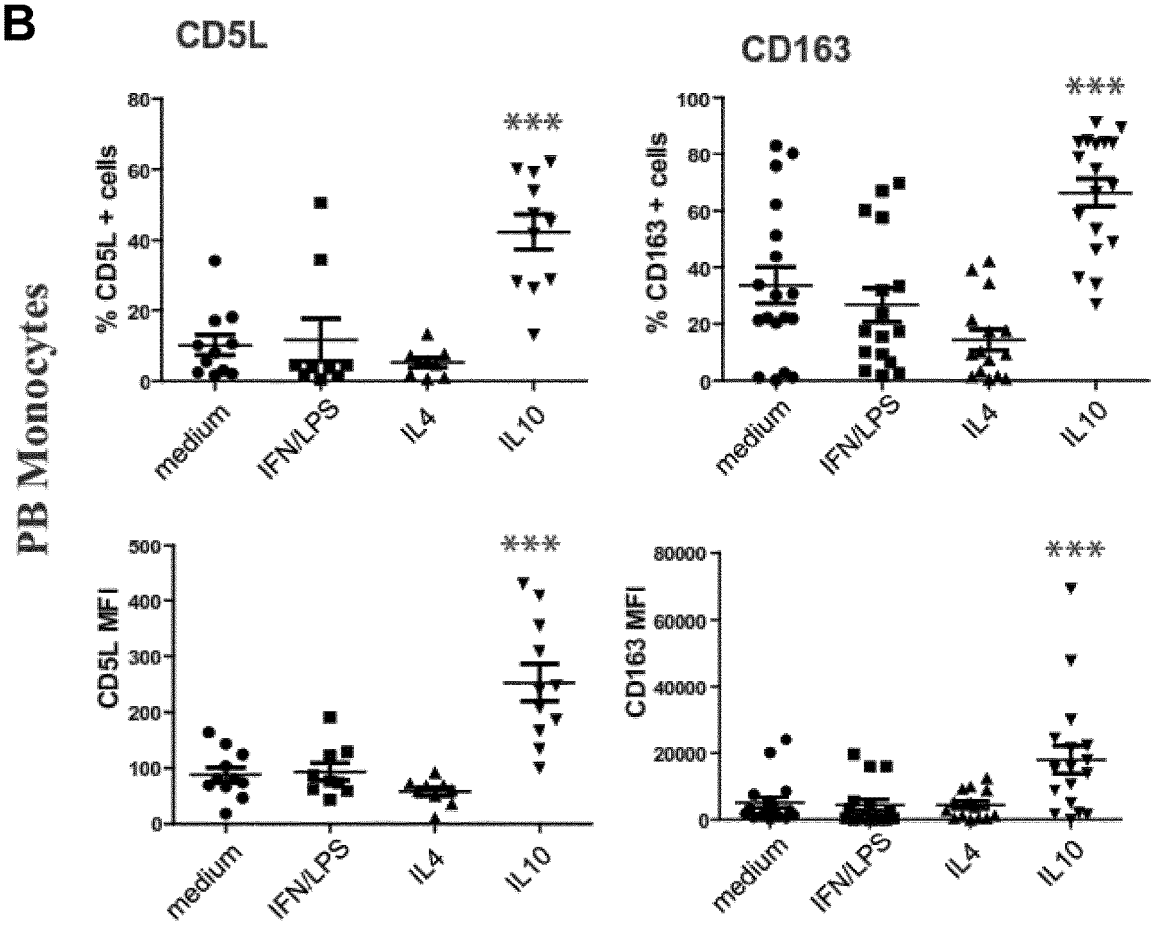

However, IFN/LPS, and to a greater extent IL10, were strong inducers of CD5L mRNA (FIG. 1 A). As for CD5L protein levels, IL10 was capable of producing a significant increase (FIG. 1 B).

In addition, liver cancer conditioned medium (CM) enhanced CD5L mRNA levels, being the CM from Huh7 cells the most potent inducer.

Interestingly, although CD5L has been described to be a secreted protein, the inventors detected its presence on macrophage's surface by flow cytometry with two different monoclonal antibodies (4D7 and 1C8 Novus biologicals) (FIG. 1 B).

Cell surface CD5L levels were positive in M2 macrophages (i.e., those polarized with IL10 and Liver cancer cell CM). In these assays, expression of CD163 was used as positive control, given that this marker is a gold standard marker for M2 macrophages. Remarkably, cell surface CD5L detection improved that of CD163 in distinguishing untreated versus IL10 or liver cancer CM-polarized macrophages, both at the percentage of positive cells (FIG. 1 B, panels above) and at their fluorescence intensity (FIG. 1 B, panels below).

Therefore, these results indicate that CD5L can be used as a cell surface marker of M2 polarized macrophages, which is even more specific than the currently used marker—CD163.

CD5L Induces M2 Macrophage Polarization

Given that a high expression of CD5L was observed in M2 macrophages, the inventors next tested whether CD5L itself was able to induce this cellular phenotype. As observed in FIG. 2, addition of recombinant human CD5L (rhCD5L) to primary cell cultures (i.e. PB monocytes) promoted an increased expression of CD163 in these cells, as compared to cells untreated (M) or treated with albumin (hSA). Therefore, CD5L is an active molecular player in the acquisition of the M2-like molecular and functional phenotype.

Figure 2:
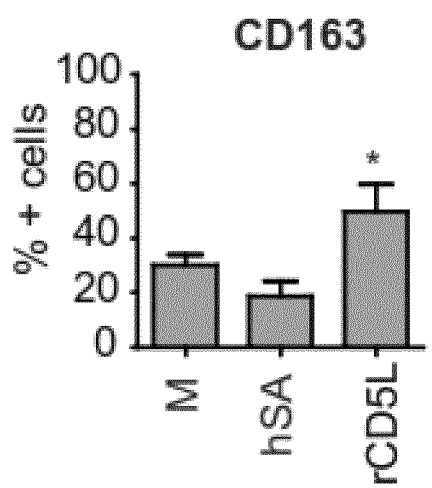
FIG. 2. (A) is a bar diagram depicting the percentage of PB monocytes positive for the M2 macrophage surface marker CD163 after treatment with normal medium (M), human albumin (hSA), or recombinant CD5L (rCD5L). (B) shows various bar diagrams depicting the TNFα or IL6 production by unstimulated or LPS-stimulated PB macrophages after treatment with control medium (M), human albumin (hSA) or recombinant CD5L (rCD5L). Statistical differences were analyzed with t-test vs M. *$p<0.05$, $p<0.01$, *$p<0.001$, FIG. 3. (A) shows various bar diagrams depicting the mRNA expression levels of several macrophage activation markers in PB macrophages after subjecting them to the treatments indicated. In these experiments, gene expression values were normalized to the expression levels of Glyceraldehyde 3-phosphate dehydrogenase (GAPDH). Columns correspond to untreated cells. Dashed columns correspond to cells not treated; black columns correspond to cells treated with IL 10; white columns with the name "isotype" correspond to the treatment with IL10 together with a control antibody that has the same isotype as the anti-CD5L antibody of the invention (i.e. IgG2a); and white columns with the name "4D7" correspond to cells treated with IL10 together with the monoclonal anti-CD5L antibody of the invention. The y-axis represents the fold change increase of mRNA levels after each treatment in comparison to IL 10 treated cells; n=4. (B) shows a bar diagram depicting the TNF produced and secreted by PB macrophages after subjecting them to the treatments indicated. Black columns correspond to untreated cells; dashed columns correspond to cells treated with a control antibody that has the same isotype as the anti-CD5L antibody of the invention (i.e. IgG2a); and white columns correspond to cells treated with the monoclonal anti-CD5L antibody of the invention (4D7). PB monocytes were further treated with IL10, LPS, or both; n=4. Statistical differences were analyzed with t test, 4D7 vs Isotype.*$p<0.05$.
Figure 2:
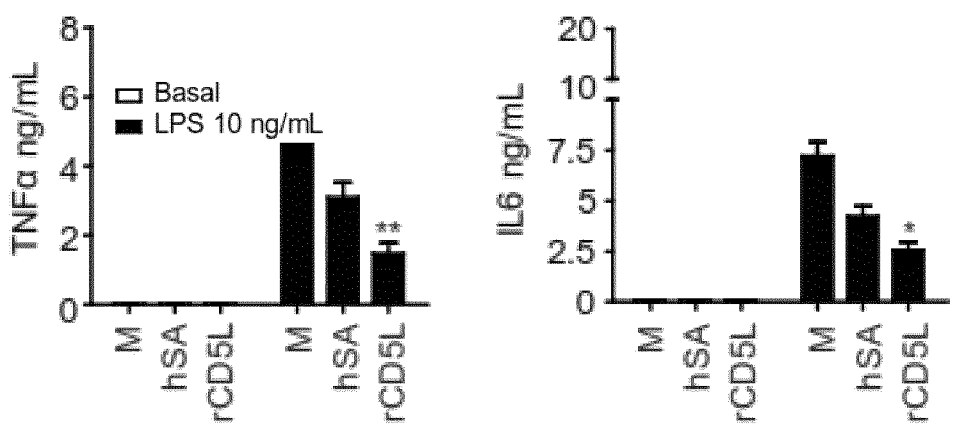

Moreover, it was found that rhCD5L was able to inhibit the TNFalpha and IL6 secretion of LPS stimulated macrophages (FIG. 2 B).

Anti-CD5L Antibodies Inhibit Macrophage M2 Activation

Given that CD5L induces M2 polarization, and it is overexpressed in IL-10 as well as liver cancer CM-polarized macrophages, the inventors next tested whether inhibition of CD5L with an antibody would affect IL10 (M2) polarization.

In these experiments, PB monocytes were cultured in a medium with or without IL10 in the presence of an anti-CD5L monoclonal antibody (4D7) or a control isotype antibody.

Figure 3:
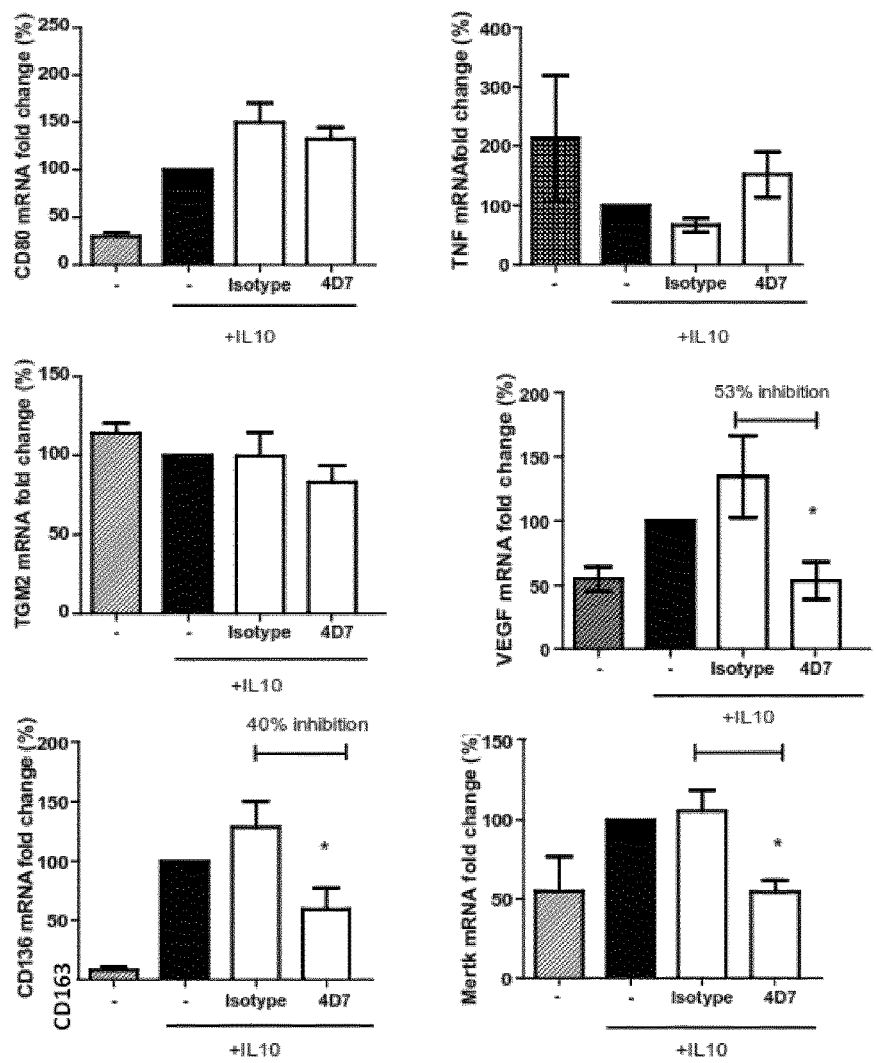
Figure 3:
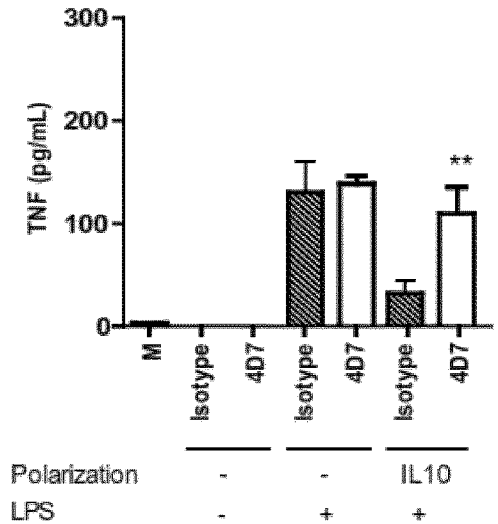

Then, mRNA levels of macrophage polarization markers CD80, TNF, TGM2, CD163, MertK, VEGF were measured (FIG. 3 A).

The results showed that incubation with an anti-CD5L antibody does not affect mRNA levels of M1 markers CD80 or TGM2.

Interestingly, however, the anti-CD5L antibody was able to strongly inhibit the IL10-mediated enhancement of M2 markers CD163, Mertk and VEGF, as compared to the isotype control antibody (FIG. 3 A). This inhibition was of 40% in the case of CD163, 48% in the case of Mertk, and 53% for VEGF.

From this data it can be concluded that an anti-CD5L monoclonal antibody, such as 4D7, and any agent other agent with the ability of binding to CD5L can be used as potent inhibitor of M2 macrophage activation.

Anti-CD5L Antibodies Restore Macrophages Pro-Inflammatory Activity

Given that anti-CD5L antibodies were able to inhibit M2 activation, the inventors next tested whether said antibodies could restore the inflammatory response of M2 activated macrophages.

For that purpose, the inflammatory response of IL10 activated macrophages was analyzed by measuring their tumor necrosis factor alpha (TNF) response to lipopolysaccharide (LPS), a known inflammatory activator. In these experiments, IL10 polarization induced a far lower TNF response to LPS (FIG. 3 B). Strikingly, addition of anti-CD5L antibodies (4D7) restored the secretion of LPS to normal levels, confirming the notion that blocking CD5L can be used to inhibit the activity and phenotype of M2 (anti-inflammatory) macrophages.

CD5L is Expressed in Tumor Macrophages and its Increased Levels are Associated with Bad Prognosis in Hepatocellular Carcinoma (HCC)

To assess liver macrophage expression of CD5L in HCC, IF staining was performed in TMAs, which included n=60 HCC tumor (T)/44 adjacent liver (NT).

Figure 4:
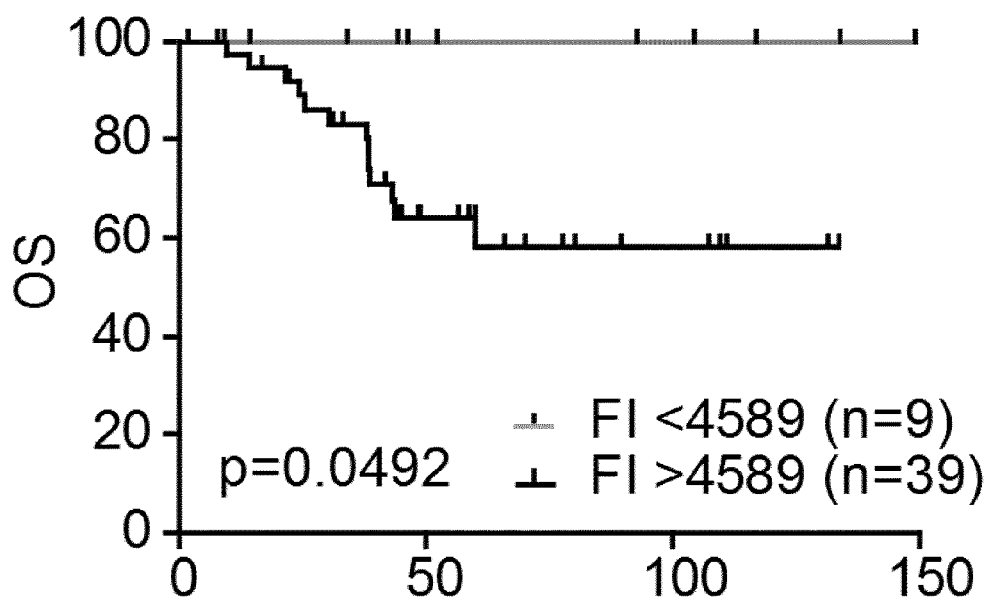
FIG. 4 is a graph depicting the Overall Survival (OS) of patients suffering from hepatocellular carcinoma (HCC), according to the percentage of CD68+CD5L+ macrophages found in the tumor. The y-axis represents the percentage of surviving patients, and the x-axis the time in months. (a) represents patients where the percentage of CD5L+CD68+ macrophages in the tumor tissue is lower than 50%, and (b) represents patients where the percentage of CD5L+CD68+ macrophages in the tumor tissue is higher than 50%. Statistical differences were analyzed with the Kaplan-Meier's method and log rank test were performed to compare differences among curves; n=48, p=0.0492.

In these studies, macrophages were detected with antibodies against CD68 (rabbit anti-human CD68, SIGMA) and CD5L (4D7). Interestingly, patients with less than 50% of CD5L+ macrophages in the tumor tissue had better Overall Survival (OS) than those with more than 50% of CD5L+ macrophages rank (FIG. 4). These results suggest that increased expression of CD5L in tumor macrophages is associated to worse prognosis.

Immunotherapy Targeting CD5L Arrests Tumor Growth

Figure 5:
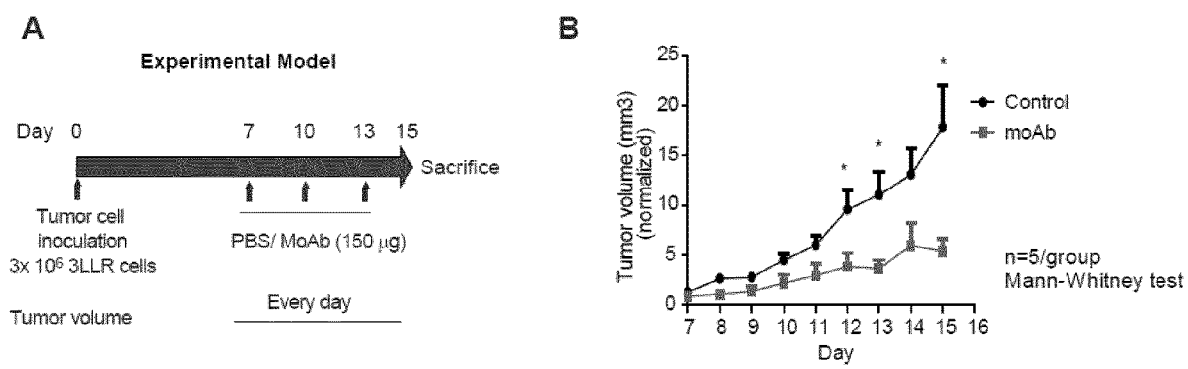
FIG. 5. Anti-CD5L moAb treatment inhibits tumor growth (A) Schematic illustration of the LLC lung tumor model and moAb treatment regimen.

We next assessed whether CD5L could be used as a target for immunotherapy. Wild-type mice were injected with Lewis-Lung Carcinoma (LLC) cells subcutaneously in the flanks of n=5 mice, and a CD5L specific moAb D7 was given intraperitoneally (i.p.) every 3 days followed by monitoring of tumor growth. Control animals were given the same volume of PBS. We found that LLC tumor-bearing mice that were treated with anti-CD5L moAb D7 had smaller tumors measured as tumor volume, compared to PBS-injected mice (see FIG. 5).

rhCD5L Inhibits T Cell Proliferation

To assess whether rhCD5L affects T cell biology, we determined whether addition of rhCD5L could modify T cell proliferation in response to a polyclonal stimulus. To this end, T cells were stimulated with CD2/3/28 beads in the presence or absence of rhCD5L. As observed in FIG. 6, presence of rhCD5L reduced T cell proliferation (A), without affecting viability (B).

CITATION LIST

WO9839443

Mantovani A. et al., "Macrophages, innate immunity and cancer: balance, tolerance, and diversity", Curr Opin Immunol. 2010 April; 22(2):231-7.

Altschul, S. F. et. al., "Gapped BLAST and PSI-BLAST: a new generation of protein database search programs", Nucleic Acids Research—1997, Vol. No. 25, pp.: 3389-3402.

Burtis C. A. et al., Chapter 14, section "Statistical Treatment of Reference Values", 2008.

Sanjurjo L. et al., "The human CD5L/AIM-CD36 axis: A novel autophagy inducer in macrophages that modulates inflammatory responses", Autophagy. Taylor and Francis Inc.; 2015; 11(3):487-502

Amézaga N. et al., "Human scavenger protein AIM increases foam cell formation and CD36-mediated oxLDL uptake", J Leukoc Biol. 2014; 95(3):509-20.

Sanjurjo L, et al., "The human CD5L/AIM-CD36 axis: A novel autophagy inducer in macrophages that modulates inflammatory responses". Autophagy. Taylor and Francis Inc.; 2015; 11(3):487-502.

Amézaga N, et al., "Human scavenger protein AIM increases foam cell formation and CD36-mediated oxLDL uptake". J Leukoc Biol. 2014; 95(3):509-20

Galfre G, Howe S C, Milstein C, Butcher G W, Howard J C. "Antibodies to major histocompatibility antigens produced by hybrid cell lines". Nature. 1977; 266:550-552.

Harlow E. and Lane D. E. "Antibodies: A Laboratory Manual". Cold Spring Harbor, New York: Cold Spring Harbor Laboratory Press, 1988.

Kashmiri S V et al., "SDR grafting—a new approach to antibody humanization" Methods. 2005, vol. 36(1), pp. 25-34.

Kostelny S A. et al., "Formation of a bispecific antibody by the use of leucine zippers", J Immunol. 1992, vol. 148(5), pp. 1547-53.

Presta L G et al., "Antibody engineering", Curr Opin Biotechnol. 1992, vol. 3(4), pp. 394-8.

Safdari Y. et al., "Antibody humanization methods—a review and update", Biotechnol Genet Eng Rev. 2013, vol. 29, pp. 175-86.

The invention claimed is:

1. A method of inhibiting the immunosuppressive M2 phenotype in macrophages in a mammal in need thereof, the method comprising: administering to the mammal a pharmaceutical composition comprising a therapeutically effective amount of a CD5L-binding agent capable of inhibiting the immunosuppressive M2 phenotype in macrophages, together with one or more pharmaceutically acceptable carriers or excipients;

wherein the CD5L-binding agent is an anti-CD5L monoclonal antibody capable of inhibiting the immunosuppressive M2 phenotype in macrophages, wherein said anti-CD5L monoclonal antibody comprises:

a. a VH sequence comprising, in the following specified order, a CDR1 of sequence consisting of SEQ ID NO: 3, a CDR2 of sequence consisting of SEQ ID NO: 4, and a CDR3 of sequence consisting of SEQ ID NO: 1; and b. a VL sequence comprising, in the following specified order, a CDR1 of sequence consisting of SEQ ID NO: 5, a CDR2 of sequence consisting of SEQ ID NO: 6, and a CDR3 of sequence consisting of SEQ ID NO: 2.

2. The method of claim 1, wherein the method produces a pro-inflammatory response in the mammal.

3. The method of claim 1, wherein the method is an immunotherapy method for treatment of cancer.

4. The method of claim 3, wherein the cancer is selected from the group consisting of: papillomas, adenomas, lipomas, osteomas, myomas, angiomas, nevi, mature teratomas, carcinomas, sarcomas, immature teratomas, melanoma, myeloma, leukemia, Hodgkin's lymphoma, basalioma, spinalioma, breast cancer, ovarian cancer, uterine cancer, lung cancer, bronchial cancer, prostate cancer, colon cancer, pancreatic cancer, kidney cancer, esophageal cancer, hepatocellular carcinoma (HCC), and head and neck cancer.

5. A kit comprising:
   (a) a CD5L-binding agent, wherein the CD5L-binding agent is an anti-CD5L monoclonal antibody capable of inhibiting the immunosuppressive M2 phenotype in macrophages, wherein said anti-CD5L monoclonal antibody comprises:
      a. the VH sequence comprises, in the following specified order, a CDR1 of sequence consisting of SEQ ID NO: 3, a CDR2 of sequence consisting of SEQ ID NO: 4, and a CDR3 of sequence consisting of SEQ ID NO: 1; and
      b. the VL sequence comprises, in the following specified order, a CDR1 of sequence consisting of SEQ ID NO: 5, a CDR2 of sequence consisting of SEQ ID NO: 6, and a CDR3 of sequence consisting of SEQ ID NO: 2; and
   (b) instructions for administering the CD5L binding agent to a mammal to induce a pro-inflammatory response and inhibit M2 activation in the mammal.

6. The kit of claim 5, wherein the administering is for cancer immunotherapy.

7. A method of inhibiting the immunosuppressive M2 phenotype in macrophages in a mammal in need thereof, the method comprising: administering to the mammal a pharmaceutical composition comprising a therapeutically effective amount of a CD5L-binding agent capable of inhibiting the immunosuppressive M2 phenotype in macrophages, together with one or more pharmaceutically acceptable carriers or excipients;
   wherein the CD5L-binding agent is an anti-CD5L monoclonal antibody capable of inhibiting the immunosuppressive M2 phenotype in macrophages;
   wherein said anti-CD5L monoclonal antibody comprises:
   a. a heavy chain consisting of SEQ ID NO: 9; and
   b. a light chain consisting of SEQ ID NO: 10.

8. The method of claim 7, wherein the method produces a pro-inflammatory response in the mammal.

9. The method of claim 7, wherein the method is an immunotherapy method for treatment of cancer.

10. The method of claim 9, wherein the cancer is selected from the group consisting of: papillomas, adenomas, lipomas, osteomas, myomas, angiomas, nevi, mature teratomas, carcinomas, sarcomas, immature teratomas, melanoma, myeloma, leukemia, Hodgkin's lymphoma, basalioma, spinalioma, breast cancer, ovarian cancer, uterine cancer, lung cancer, bronchial cancer, prostate cancer, colon cancer, pancreatic cancer, kidney cancer, esophageal cancer, hepatocellular carcinoma (HCC), and head and neck cancer.

11. A kit comprising:
   (a) a CD5L-binding agent wherein the CD5L-binding agent is an anti-CD5L monoclonal antibody capable of inhibiting the immunosuppressive M2 phenotype in macrophages;
   wherein said anti-CD5L monoclonal antibody comprises:
   a. a heavy chain consisting of SEQ ID NO: 9; and
   b. a light chain consisting of SEQ ID NO: 10; and
   (b) instructions for administering the CD5L binding agent to a mammal to induce a pro-inflammatory response and inhibit M2 activation in the mammal.

12. The kit of claim 11, wherein the administering is for cancer immunotherapy.

* * * * *

SEQUENCE LISTING

```
<160> NUMBER OF SEQ ID NOS: 34

<210> SEQ ID NO 1
<211> LENGTH: 14
<212> TYPE: PRT
<213> ORGANISM: Artificial
<220> FEATURE:
<223> OTHER INFORMATION: VH CDR3

<400> SEQUENCE: 1

Ala Arg Lys Gly Tyr Arg Tyr Asp Gly Tyr Ala Met Asp Tyr
1               5                   10

<210> SEQ ID NO 2
<211> LENGTH: 9
<212> TYPE: PRT
<213> ORGANISM: Artificial
<220> FEATURE:
<223> OTHER INFORMATION: VL CDR3

<400> SEQUENCE: 2

Gln Gln His Tyr Gly Ser Pro Leu Thr
1               5

<210> SEQ ID NO 3
<211> LENGTH: 8
<212> TYPE: PRT
<213> ORGANISM: Artificial
<220> FEATURE:
<223> OTHER INFORMATION: VH CDR1

<400> SEQUENCE: 3

Gly Tyr Ser Phe Thr Gly Tyr Asn
1               5

<210> SEQ ID NO 4
<211> LENGTH: 8
<212> TYPE: PRT
<213> ORGANISM: Artificial
<220> FEATURE:
<223> OTHER INFORMATION: VH CDR2

<400> SEQUENCE: 4

Ile Asp Thr Tyr Tyr Gly Gly Ile
1               5

<210> SEQ ID NO 5
<211> LENGTH: 12
```

```
<212> TYPE: PRT
<213> ORGANISM: Artificial
<220> FEATURE:
<223> OTHER INFORMATION: VL CDR1

<400> SEQUENCE: 5

Gln Ser Leu Leu Asn Ser Asn Asn Gln Lys Asn Tyr
1               5                   10

<210> SEQ ID NO 6
<211> LENGTH: 3
<212> TYPE: PRT
<213> ORGANISM: Artificial
<220> FEATURE:
<223> OTHER INFORMATION: VL CDR2

<400> SEQUENCE: 6

Phe Ala Ser
1

<210> SEQ ID NO 7
<211> LENGTH: 121
<212> TYPE: PRT
<213> ORGANISM: Artificial
<220> FEATURE:
<223> OTHER INFORMATION: VH

<400> SEQUENCE: 7

Glu Val Gln Leu Gln Gln Ser Gly Pro Glu Leu Ala Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Thr Tyr Tyr Gly Gly Ile Ser Tyr Asn Gln Lys Phe
    50                  55                  60

Lys Asp Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Lys Gly Tyr Arg Tyr Asp Gly Tyr Ala Met Asp Tyr Trp Gly
            100                 105                 110

Gln Gly Thr Ser Val Thr Val Ser Ser
            115                 120

<210> SEQ ID NO 8
<211> LENGTH: 113
<212> TYPE: PRT
<213> ORGANISM: Artificial
<220> FEATURE:
<223> OTHER INFORMATION: VL

<400> SEQUENCE: 8

Asp Ile Val Met Thr Gln Ser Pro Ser Ser Leu Ser Met Ser Val Gly
1               5                   10                  15

Gln Lys Val Thr Met Asn Cys Lys Ser Ser Gln Ser Leu Leu Asn Ser
            20                  25                  30

Asn Asn Gln Lys Asn Tyr Leu Ala Trp Tyr Gln Gln Lys Pro Gly Gln
        35                  40                  45

Ser Pro Lys Leu Leu Leu Tyr Phe Ala Ser Thr Arg Lys Ser Gly Val
    50                  55                  60
```

```
Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
            85                  90                  95

His Tyr Gly Ser Pro Leu Thr Phe Gly Ala Gly Thr Lys Leu Glu Leu
        100                 105                 110

Lys
```

<210> SEQ ID NO 9
<211> LENGTH: 470
<212> TYPE: PRT
<213> ORGANISM: Artificial
<220> FEATURE:
<223> OTHER INFORMATION: Heavy chain

<400> SEQUENCE: 9

```
Met Glu Trp Ile Trp Val Phe Leu Phe Leu Leu Ser Gly Thr Ala Gly
1               5                   10                  15

Val His Ser Glu Val Gln Leu Gln Gln Ser Gly Pro Glu Leu Ala Lys
            20                  25                  30

Pro Gly Ala Ser Val Lys Ile Ser Cys Lys Ala Ser Gly Tyr Ser Phe
        35                  40                  45

Thr Gly Tyr Asn Met Asn Trp Val Lys Gln Ser Asn Gly Lys Ser Leu
    50                  55                  60

Glu Trp Ile Gly Asn Ile Asp Thr Tyr Tyr Gly Ile Ser Tyr Asn
65                  70                  75                  80

Gln Lys Phe Lys Asp Lys Ala Thr Leu Thr Val Asp Lys Ser Ser Ser
            85                  90                  95

Thr Ala Tyr Met Gln Leu Lys Ser Leu Thr Ser Glu Asp Ser Ala Val
        100                 105                 110

Tyr Tyr Cys Ala Arg Lys Gly Tyr Arg Tyr Asp Gly Tyr Ala Met Asp
    115                 120                 125

Tyr Trp Gly Gln Gly Thr Ser Val Thr Val Ser Ser Ala Lys Thr Thr
130                 135                 140

Ala Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
            165                 170                 175

Val Thr Leu Thr Trp Asn Ser Gly Ser Leu Ser Ser Gly Val His Thr
        180                 185                 190

Phe Pro Ala Val Leu Gln Ser Asp Leu Tyr Thr Leu Ser Ser Ser Val
    195                 200                 205

Thr Val Thr Ser Ser Thr Trp Pro Ser Gln Ser Ile Thr Cys Asn Val
210                 215                 220

Ala His Pro Ala Ser Ser Thr Lys Val Asp Lys Lys Ile Glu Pro Arg
225                 230                 235                 240

Gly Pro Thr Ile Lys Pro Cys Pro Pro Cys Lys Cys Pro Ala Pro Asn
            245                 250                 255

Leu Leu Gly Gly Pro Ser Val Phe Ile Phe Pro Pro Lys Ile Lys Asp
        260                 265                 270

Val Leu Met Ile Ser Leu Ser Pro Ile Val Thr Cys Val Val Val Asp
    275                 280                 285

Val Ser Glu Asp Asp Pro Asp Val Gln Ile Ser Trp Phe Val Asn Asn
290                 295                 300

Val Glu Val His Thr Ala Gln Thr Gln Thr His Arg Glu Asp Tyr Asn
```

```
                305                 310                 315                 320
Ser Thr Leu Arg Val Val Ser Ala Leu Pro Ile Gln His Gln Asp Trp
                    325                 330                 335

Met Ser Gly Lys Glu Phe Lys Cys Lys Val Asn Asn Lys Asp Leu Pro
                340                 345                 350

Ala Pro Ile Glu Arg Thr Ile Ser Lys Pro Lys Gly Ser Val Arg Ala
                355                 360                 365

Pro Gln Val Tyr Val Leu Pro Pro Glu Glu Met Thr Lys Lys
                370                 375                 380

Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
                    405                 410                 415

Thr Glu Pro Val Leu Asp Ser Asp Gly Ser Tyr Phe Met Tyr Ser Lys
                420                 425                 430

Leu Arg Val Glu Lys Lys Asn Trp Val Glu Arg Asn Ser Tyr Ser Cys
                435                 440                 445

Ser Val Val His Glu Gly Leu His Asn His His Thr Thr Lys Ser Phe
                450                 455                 460

Ser Arg Thr Pro Gly Lys
465                 470

<210> SEQ ID NO 10
<211> LENGTH: 240
<212> TYPE: PRT
<213> ORGANISM: Artificial
<220> FEATURE:
<223> OTHER INFORMATION: Light chain

<400> SEQUENCE: 10

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ser
                20                  25                  30

Met Ser Val Gly Gln Lys Val Thr Met Asn Cys Lys Ser Ser Gln Ser
            35                  40                  45

Leu Leu Asn Ser Asn Asn Gln Lys Asn Tyr Leu Ala Trp Tyr Gln Gln
        50                  55                  60

Lys Pro Gly Gln Ser Pro Lys Leu Leu Leu Tyr Phe Ala Ser Thr Arg
65                  70                  75                  80

Lys Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
                100                 105                 110

Phe Cys Gln Gln His Tyr Gly Ser Pro Leu Thr Phe Gly Ala Gly Thr
            115                 120                 125

Lys Leu Glu Leu Lys Arg Ala Asp Ala Ala Pro Thr Val Ser Ile Phe
        130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
                180                 185                 190

Asp Ser Lys Asp Ser Thr Tyr Ser Met Ser Ser Thr Leu Thr Leu Thr
```

```
                195                 200                 205
Lys Asp Glu Tyr Glu Arg His Asn Ser Tyr Thr Cys Glu Ala Thr His
    210                 215                 220

Lys Thr Ser Thr Ser Pro Ile Val Lys Ser Phe Asn Arg Asn Glu Cys
225                 230                 235                 240
```

```
<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
ctgcctgacc tactgctttg                                               20

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
ggcgtacact ttcccttctc                                               20

<210> SEQ ID NO 13
<211> LENGTH: 21
<212> TYPE: DNA
<213> ORGANISM: Artificial
<220> FEATURE:
<223> OTHER INFORMATION: Primer

<400> SEQUENCE: 13
gaggaggcgc tccccaagaa g                                             21

<210> SEQ ID NO 14
<211> LENGTH: 21
<212> TYPE: DNA
<213> ORGANISM: Artificial
<220> FEATURE:
<223> OTHER INFORMATION: Primer

<400> SEQUENCE: 14
gtgaggagca catgggtgga g                                             21

<210> SEQ ID NO 15
<211> LENGTH: 21
<212> TYPE: DNA
<213> ORGANISM: Artificial
<220> FEATURE:
<223> OTHER INFORMATION: Primer

<400> SEQUENCE: 15
cctcgtggag ccagttatca a                                             21

<210> SEQ ID NO 16
<211> LENGTH: 22
<212> TYPE: DNA
<213> ORGANISM: Artificial
<220> FEATURE:
<223> OTHER INFORMATION: Primer

<400> SEQUENCE: 16
gtctgggatc tccaccgtct tc                                            22
```

```
<210> SEQ ID NO 17
<211> LENGTH: 22
<212> TYPE: DNA
<213> ORGANISM: Artificial
<220> FEATURE:
<223> OTHER INFORMATION: Primer

<400> SEQUENCE: 17
caccagttct cttggaggaa ca                                              22

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
tttcacttcc actctcccgc                                                 20

<210> SEQ ID NO 19
<211> LENGTH: 21
<212> TYPE: DNA
<213> ORGANISM: Artificial
<220> FEATURE:
<223> OTHER INFORMATION: Primer

<400> SEQUENCE: 19
ctctggcgta gagctatcac t                                               21

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
aggctgggtt ggtgaaaaca                                                 20

<210> SEQ ID NO 21
<211> LENGTH: 19
<212> TYPE: DNA
<213> ORGANISM: Artificial
<220> FEATURE:
<223> OTHER INFORMATION: Primer

<400> SEQUENCE: 21
tcttcttttg cgtcgccag                                                  19

<210> SEQ ID NO 22
<211> LENGTH: 17
<212> TYPE: DNA
<213> ORGANISM: Artificial
<220> FEATURE:
<223> OTHER INFORMATION: Primer

<400> SEQUENCE: 22
agccccagcc ttctcca                                                    17

<210> SEQ ID NO 23
<211> LENGTH: 20
<212> TYPE: DNA
<213> ORGANISM: Artificial
<220> FEATURE:
```

<223> OTHER INFORMATION: Primer

<400> SEQUENCE: 23
agctcatcac cttcacctgc                                          20

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
cccagagcag aggttgtctc                                          20

<210> SEQ ID NO 25
<211> LENGTH: 21
<212> TYPE: DNA
<213> ORGANISM: Artificial
<220> FEATURE:
<223> OTHER INFORMATION: Primer

<400> SEQUENCE: 25
agggcagaat catcacgaag t                                        21

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26
agggtctcga ttggatggca                                          20

<210> SEQ ID NO 27
<211> LENGTH: 20
<212> TYPE: DNA
<213> ORGANISM: Artificial
<220> FEATURE:
<223> OTHER INFORMATION: Primer

<400> SEQUENCE: 27
cagtggatag acagatgggg                                          20

<210> SEQ ID NO 28
<211> LENGTH: 31
<212> TYPE: DNA
<213> ORGANISM: Artificial
<220> FEATURE:
<223> OTHER INFORMATION: Primer

<400> SEQUENCE: 28
gggaattcga ggtgcagctg caggagtctg g                             31

<210> SEQ ID NO 29
<211> LENGTH: 22
<212> TYPE: DNA
<213> ORGANISM: Artificial
<220> FEATURE:
<223> OTHER INFORMATION: Primer

<400> SEQUENCE: 29
ctgggtcttt ctcttcctcc tg                                       22

```
<210> SEQ ID NO 30
<211> LENGTH: 22
<212> TYPE: DNA
<213> ORGANISM: Artificial
<220> FEATURE:
<223> OTHER INFORMATION: Primer

<400> SEQUENCE: 30
cgtacctata gccctttctt gc                                              22

<210> SEQ ID NO 31
<211> LENGTH: 28
<212> TYPE: DNA
<213> ORGANISM: Artificial
<220> FEATURE:
<223> OTHER INFORMATION: Primer

<400> SEQUENCE: 31
gggaattcac tggatggtgg gaagatgg                                        28

<210> SEQ ID NO 32
<211> LENGTH: 32
<212> TYPE: DNA
<213> ORGANISM: Artificial
<220> FEATURE:
<223> OTHER INFORMATION: Primer

<400> SEQUENCE: 32
gggagctcga yattgtgmts acmcarwctm ca                                   32

<210> SEQ ID NO 33
<211> LENGTH: 21
<212> TYPE: DNA
<213> ORGANISM: Artificial
<220> FEATURE:
<223> OTHER INFORMATION: Primer

<400> SEQUENCE: 33
gaatcacaga cccaggtcct c                                               21

<210> SEQ ID NO 34
<211> LENGTH: 20
<212> TYPE: DNA
<213> ORGANISM: Artificial
<220> FEATURE:
<223> OTHER INFORMATION: Primer

<400> SEQUENCE: 34
acgtgagcgg agagccataa                                                 20
```